United States Patent
Head et al.

(10) Patent No.: US 10,036,036 B1
(45) Date of Patent: Jul. 31, 2018

(54) COMPOSITIONS AND METHODS FOR DEPLOYING A TRANSGENIC REFUGE AS A SEED BLEND

(75) Inventors: Graham Head, St. Louis, MO (US); Jay C. Pershing, Webster Groves, MO (US); John K. Soteres, Olivette, MO (US)

(73) Assignee: Monsanto Technology LLC, St. Louis, MO (US)

(*) Notice: Subject to any disclaimer, the term of this patent is extended or adjusted under 35 U.S.C. 154(b) by 2818 days.

(21) Appl. No.: 11/686,725

(22) Filed: Mar. 15, 2007

(51) Int. Cl.
C12N 15/82 (2006.01)

(52) U.S. Cl.
CPC .................. C12N 15/8286 (2013.01)

(58) Field of Classification Search
None
See application file for complete search history.

(56) References Cited

U.S. PATENT DOCUMENTS

| | | | |
|---|---|---|---|
| 4,766,203 A | 8/1988 | Krieg et al. | 424/93.461 |
| 4,797,279 A | 1/1989 | Karamata et al. | 424/93.2 |
| 4,910,016 A | 3/1990 | Gaertner et al. | 424/93.461 |
| 5,633,435 A * | 5/1997 | Barry et al. | 800/288 |
| 5,659,123 A | 8/1997 | Van Rie et al. | |
| 5,696,144 A | 12/1997 | Royalty et al. | 514/404 |
| 5,753,507 A * | 5/1998 | Ohta et al. | 435/419 |
| 5,849,320 A | 12/1998 | Turnblad et al. | 424/410 |
| 5,876,739 A | 3/1999 | Turnblad et al. | 424/428 |
| 5,877,012 A | 3/1999 | Estruch et al. | 435/252.3 |
| 5,990,395 A * | 11/1999 | Plaisted et al. | 800/320.1 |
| 6,023,013 A * | 2/2000 | English et al. | 800/302 |
| 6,060,594 A | 5/2000 | English et al. | 536/23.71 |
| 6,063,597 A | 5/2000 | English et al. | 435/69.1 |
| 6,083,499 A | 7/2000 | Narva et al. | |
| 6,172,281 B1 * | 1/2001 | Van Mellaert et al. | 800/302 |
| 6,551,962 B1 * | 4/2003 | Pershing et al. | 504/100 |
| 2003/0186813 A1 | 10/2003 | Pershing et al. | 504/100 |
| 2008/0226753 A1 | 9/2008 | Cosgrove | 800/302 |
| 2009/0041869 A1 | 2/2009 | Cosgrove | 424/725 |
| 2010/0022390 A1 | 1/2010 | Cosgrove | |
| 2010/0029725 A1 | 2/2010 | Cosgrove et al. | |
| 2010/0179196 A1 | 7/2010 | Pershing et al. | |
| 2014/0366786 A1 | 12/2014 | Carroll et al. | |

FOREIGN PATENT DOCUMENTS

| | | |
|---|---|---|
| WO | WO 97/40162 | 10/1997 |
| WO | WO 98/13498 | 4/1998 |
| WO | WO 98/27218 | 6/1998 |
| WO | WO 99/31248 * | 6/1999 |
| WO | WO 99/35910 * | 7/1999 |
| WO | WO 99/35913 | 7/1999 |
| WO | WO 2005/094340 A2 | 10/2005 |
| WO | WO 2008/080166 | 7/2008 |
| WO | WO 2009/132850 | 11/2009 |
| WO | WO 2009/149787 | 12/2009 |

OTHER PUBLICATIONS

Cohen et al (Aug. 2000, International Rice Research Notes 25:4-10).*
Whalon et al (1998, Bacillus thuringiensis: Use and Resistance Management, In: "Insecticides with novel modes of action: mechanism and application", Ishaaya et al, Eds., Springer, Berlin, pp. 106-137).*
Davis et al (2000, J. Econ. Ent. 93:937-948).*
Lambert et al (1996, Proceedings/Beltwide Cotton Conference 2:931-935).*
Roush 1997, In: "Advances in Insect Control: The Role of Transgenic Plants", N. Carozzi et al, eds. Taylor and Francis, London, pp. 271-294, see p. 283, paragraph 4.*
Zhao et al (2003, Nature Biotechnol. 21:1493-1497).*
Gould et al (1998, Ann. Rev. Entomol. 43:701-726).*
Kennedy et al (1995, J. Econ. Entomol. 88:454-460).*
Office Action regarding U.S. Appl. No. 10/780,151, dated Jun. 29, 2010.
Office Action regarding U.S. Appl. No. 10/599,307, dated Jan. 7, 2009.
Roush, "Two-toxin strategies for management of insecticidal transgenic crops: can pyramiding succeed where pesticide mixtures have not?" The Royal Society, Phil. Trans. R. Soc. Loud., B 353:1777-1786, 1998.
Zhao et at, "Transgenic plants expressing two bacillus thuringiensis toxins delay insect resistance evolution," Nature Biotechnology, 21(12):1493-1497, 2003.
Agi et al., "Arthropod management: efficacy of seed mixes of transgenic Bt and nontransgenic cotton against bollworm Helicoverpa zea boddie," J. Cotton Sci., 5:74-80, 2001.
U.S. Appl. No. 10/394,929, filed Mar. 19, 2003, Pershing et al.
U.S. Appl. No. 10/780,151, filed Feb. 17, 2004, Pershing et al.
Armstrong et al., "Field evaluation of European corn borer in progeny of 173 transgenic corn event expressing an insecticidal protein from Bacillus thuringiensis," Crop Sci., 35(2):550-557, 1995.
Bates et al., "Insect resistance management in GM crops: past, present and future," Nature Biotechnol., 23:57-62, 2005.
Jansens et al., "Transgenic corn expressing a Cry9C insecticidal protein from Bacillus thuringiensis protected from European corn borer damage," Crop Sci., 37(5):1616-1624, 1997.
Li et al., "Effects of Bt cotton expressing Crylac and Cry2ab and non-Bt cotton on behavior, survival and development of trichoplusia ni (Lepidoptera:noctuidae)," Crop Protect J., 25-940948, 2006.
Mallet et al., "Preventing insect adaptation to insect-resistant crops: are seed mixtures or refugia the best strategy?," Proc. R. Soc. Lond. B, 250:165-169, 1992.
Moellenbeck et al., "Insecticidal proteins from Bacillus thuringiensis protect corn from corn rootworms," Nature Biotechnology, 19:668-672, 2001.
Ostlie, "Crafting crop resistance to corn rootworms," Nature Biotechnology, 19:624,625, 2001.

(Continued)

Primary Examiner — Anne Kubelik
(74) Attorney, Agent, or Firm — Dentons US LLP; T. K. Ball Esq.; Carine M. Doyle Esq.

(57) ABSTRACT

Methods and compositions for deploying refuge seeds together with transgenic crop seeds are provided. The refuge seeds can be non-transgenic seeds of a similar variety to that of the transgenic crop seeds, or the refuge seeds can be a transgenic variety, but in either case lacking a transgenic trait conferring pest protection found in the transgenic crop seeds.

3 Claims, No Drawings

(56) References Cited

OTHER PUBLICATIONS

Ramachandran et al., "Intraspecific competition of an insect-resistant transgenic canola in seed mixtures," *Agron. J.*, 92:368-374, 2000.
Tabashnik, "Delaying insect adaptation to transgenic plants: seedmixtures and refugia reconsidered," *Proc. Royal Soc. Lond. B*, 255(1342):7-12, 1994.
Vaughn et al., "A method of controlling corn rootworm feeding using a Bacillus thuringiensis protein expressed in transgenic maize," *Crop Sci.*, 45:931-938, 2005.
Crickmore et al., "Bacillus thuringiensis toxin nomenclature," http://www.lifesci.sussex.ac.uk/home/Neil_Crickmore/Bt, 2008.
Crickmore et al., "Revision of the nomenclature for the bacillus thuringiensis pesticidal crystal proteins," *Microbiol. Mol. Biol. Rev.*, 62:807-813, 1998.
Kennedy et al., "Managing pest resistance to bacillus thuringiensis endotoxins: constraints and incentives to implementation," *J. Econ Entomol.*, 88:454-460, 1995.
Lambert et al., "Effects of natural enemy conservation and planting date on the susceptibility of Bt cotton to helicoverpa zea in North Carolina," *Proceedings/Beltwide Cotton Conference*, 2:931-935, 1996.
Maqbool et al., "Multiple traits of agronomic importance in transgenic indica rice plants: analysis of transgene integration patterns, expression levels and stability," *Molecular Breeding* 5:471-480, 1999.
Office Action regarding U.S. Appl. No. 10/780,151, dated Mar. 26, 2008.
Response to Office Action regarding U.S. Appl. No. 10/780,151, dated Jul. 22, 2008.
Final Office Action regarding U.S. Appl. No. 10/780,151, dated Oct. 20, 2008.
Notice of Appeal regarding U.S. Appl. No. 10/780,151, dated Mar. 20, 2009.
Response to Office Action regarding U.S. Appl. No. 10/780,151, dated Sep. 18, 2009.
Request for Continued Examination regarding U.S. Appl. No. 10/780,151, dated Sep. 18, 2009.
Office Action regarding U.S. Appl. No. 10/780,151, dated Dec. 17, 2009.
Amendment and Response to Office Action regarding U.S. Appl. No. 10/780,151, dated Apr. 19, 2010.
Response to Office Action regarding U.S. Appl. No. 10/780,151, dated Mar. 7, 2011.
Request for Continued Examination regarding U.S. Appl. No. 10/780,151, dated Mar. 7, 2011.
Office Action regarding U.S. Appl. No. 12/651,174, dated Dec. 2, 2010.
Response to Office Action regarding U.S. Appl. No. 12/651,174, filed Apr. 28, 2011.
Office Action regarding U.S. Appl. No. 12/651,174, dated Jul. 12, 2011.
Response to Office Action regarding U.S. Appl. No. 12/651,174, filed Dec. 12, 2011.
Office Action regarding U.S. Appl. No. 12/651,174, filed Jan. 6, 2012.
Environmental Protection Agency (EPA), "Transmittal of the Final Report of the FIFRA Scientific Advisory Subpanel on Bacillus thuringiensis (Bt) Plant-Pesticides and Resistance Management, Meeting held on Feb. 9 and 10, 1998," http://www.epa.gov/scipoly/sap/meetings/1998/february/finalfeb.pdf.
Non-Final Office Action regarding U.S. Appl. No. 12/651,174, dated Aug. 26, 2013.
Response to Non-Final Office Action regarding U.S. Appl. No. 10/780,151, dated Sep. 9, 2014, and Declaration of Graham Head, Ph.D. Under 37 C.F.R. §1.132.
Response to Office Action regarding U.S. Appl. No. 12/651,174, dated Nov. 26, 2013.
Final Office Action regarding U.S. Appl. No. 12/651,174, dated Feb. 11, 2014.
Bannert et al., "Short-distance cross-pollination of maize in a small-field landscape as monitored by grain color markers," *Europ. J. Agronomy* vol. 29, pp. 29-32, 2008.
Brookes et al., 2004, "Genetically modified maize: pollen movement and crop co-existence," *PG Economics Ltd.*, Dorchester, United Kingdom (available at http://www.pgeconomics.co.uk).
Burkness et al., "Cross-pollination of nontransgenic corn ears with transgenic bt corn: efficacy against lepidopteran pests and implications for resistance management," *Journal of Economic Entomology*, vol. 104, No. 5, pp. 1476-1479, 2011.
Burkness et al., "Bt pollen dispersal and bt kernel mosaics: integrity of non-bt refugia for lepidopteran resistance management in maize," *Journal of Economic Entomology*, vol. 105, No. 5, pp. 1773-1780, 2012.
Chilcutt et al., "Contamination of refuges by bacillus thuringiensis toxin genes from transgenic maize," *PNAS*, vol. 101, No. 20, pp. 7526-7529, 2004.
Onstad et al., "Seeds of change: corn seed mixtures for resistance management and integrated pest management," Journal of Economic Entomology, vol. 104, No. 2, pp. 343-352, 2011.
Response to Office Action regarding U.S. Appl. No. 12/651,174, filed Jan. 22, 2013.
Response to Final Office Action regarding U.S. Appl. No. 12/651,174, dated Jun. 11, 2014.
USPTO: Non-Final Office Action regarding U.S. Appl. No. 10/780,151, dated Jun. 19, 2014.
Appeal Brief regarding U.S. Appl. No. 12/651,174, dated Oct. 24, 2014.
Examiner's Answer to Appeal Brief regarding U.S. Appl. No. 12/651,174, dated Dec. 5, 2014.
Final Office Action regarding U.S. Appl. No. 10/780,151, dated Dec. 16, 2014.
U.S. Appl. No. 14/304,715, filed Jun. 13, 2014, Carroll et al.
Reply Brief to Examiner's Answer to Appeal Brief regarding U.S. Appl. No. 12/651,174, dated Feb. 5, 2015.
Amendment and Response to Office Action in U.S. Appl. No. 12/651,174, dated Jun. 6, 2012.
Non-final Office Action in U.S. Appl. No. 12/651,174, dated Jul. 20, 2012.
USPTO: Examiner's Answer to Appeal Brief regarding U.S. Appl. No. 10/780,151, dated Dec. 2, 2015.
Reply to Examiner's Answer to Appeal Brief regarding U.S. Appl. No. 10/780,151, dated Feb. 2, 2016.
USPTO: Decision on Appeal regarding U.S. Appl. No. 12/651,174, dated Apr. 28, 2017.
USPTO: Notice of Allowance and Fee(s) Due regarding U.S. Appl. No. 12/651,174, dated Jul. 10, 2017.
Appeal Brief regarding U.S. Appl. No. 10/780,151, dated Jul. 16, 2015.

\* cited by examiner

COMPOSITIONS AND METHODS FOR DEPLOYING A TRANSGENIC REFUGE AS A SEED BLEND

BACKGROUND OF THE INVENTION

(1) Field of the Invention

The present invention relates generally to transgenic crops and refugia associated with the transgenic crops, and more generally to the control of pests that cause damage to crop plants, such as pests that cause damage by their feeding activities directed to roots, shoots, stems, flower parts, fruit and vegetable product parts, and leaf parts.

(2) Description of the Related Art

Insects, nematodes, and related arthropods annually destroy an estimated 15% of agricultural crops in the United States and even more than that in developing countries. In addition, competition with weeds and parasitic and saprophytic plants account for even more potential yield losses.

Some of this damage occurs in the soil when plant pathogens, insects and other such soil borne pests attack the seed after planting. In the production of corn, for example, much of the rest of the damage is caused by rootworms—insect pests that feed upon or otherwise damage the plant roots; and by cutworms, European corn borers, other pests that feed upon or damage the above ground parts of the plant, and non-crop plants such as weeds and parasitic and saprophytic plants that can deprive the crop plant of valuable moisture and soil derived nutritional potential. General descriptions of the type and mechanisms of attack of pests on agricultural crops are provided by, for example, Metcalf (1962) and Agrios (1988).

Corn is the most important grain crop in the Midwestern United States. Among the most serious insect pests of corn in this region are the larval forms of three species of *Diabrotica* beetles. These include the Western corn rootworm, *Diabrotica virgifera virgifera* LeConte, the Northern corn rootworm, *Diabrotica barberi* Smith and *Diabrotica barberi* Lawrence, and the Southern corn rootworm, *Diabrotica undecimpunctata howardi* Barber. In South America, related species including *Diabrotica speciosa* Germar and *Diabrotica viridula* Fabricius also attack crops. Corn rootworm is also becoming a significant crop pest in Europe. In fact, more chemical insecticide is used for the control of corn rootworm than for any other pest of corn, and the total acreage treated with chemical insecticides is greater than for any other pest in the United States.

Corn rootworms (CRW) overwinter in the egg stage in fields where corn was grown the previous season. The eggs hatch from late May through June. If a corn crop is not followed by another corn crop in the subsequent year, the larvae will die. Accordingly, the impact of corn rootworm is felt most directly in areas where corn is systematically followed by corn, as is typical in many areas of the Midwestern United States.

After hatching, the larvae pass through three larval stages or instars, during which they feed on the corn root system. About three weeks is required for completion of the larval stage. Damage to the corn root system caused by the feeding of larvae is the major cause of harvest losses in corn due to corn rootworm. Corn plants that fall over and lodge in the field after weakening or destruction of a major part of the root system are the cause of a major portion of this loss, since this lodged corn cannot be harvested by conventional mechanized machinery and is left in the field.

Following completion of larval development, the larvae transform into immobile pupae, and thence into the adult beetles that emerge from the soil throughout the summer, with the period of emergence depending upon the growing location. After emergence, the adult beetles feed for about two weeks before the females start laying eggs. Initially, the adults feed predominantly in the same field from which they emerged, but later will migrate to other fields. Peak adult activity normally occurs in the U.S. Corn Belt during late July or early August in fields planted to continuous corn, but activity may peak later in first year or late maturing cornfields. Rootworm beetles begin depositing eggs in cornfields approximately two weeks after they emerge. (For more information, see, e.g., *Corn Rootworms*, Field Crops Pest Management Circular #16, Ohio Pest Management & Survey Program, The Ohio State University, Extension Division, Columbus, Ohio; available online at the Ohio State web site ag.ohio-state.edu/~ohioline/icm-fact/fc-16.html; and McGahen et al., *Corn Insect Control: Corn Rootworm*, PENpages number 08801502, Factsheet available from Pennsylvania State University, State College, Pa., 1989).

There is evidence of the emergence of a new race of corn rootworm which oviposits onto adjacent soybean plants for overwintering. The most common practice in the midwestern United States has been for fields to be rotated annually with corn, followed the next year with soybeans, in order to manage the development of an epidemic of corn rootworm pressure on fields of corn. While this strategy overall has been successful in reducing the corn rootworm feeding pressure on corn in many areas, the evolutionary emergence of this new race of corn rootworm creates a problem which was not anticipated and which could not have been easily foreseen. This new race, which preferentially deposits its eggs onto soybean fields, provides an unintended feeding pressure on the next years' intended corn crop in the field in which soybeans were grown the previous year, along with the subsequent requirement for insecticidal control measures which adds unexpected costs to the farmer in the form of additional labor for spraying and additional costs of goods, further reducing the return to the farmer on his/her investment in the crop and its harvest. Other corn rootworm populations are known which undergo extended diapause, their eggs hatching only in the second growing season after their deposit, when a typical crop rotation has switched a field back to corn production, in order to circumvent the presence of the non-host plant.

One means for combating the corn rootworm pressures in the US, in particular in view of the introduction of recombinant crops containing genes which express proteins which are insecticidal to a selected few intended crop pest insect species, has been the regulatory agencies' requirement that farmers plant a non-recombinant refuge crop which provides a means for producing a steady and consistent population of adult insects which have never been exposed to the recombinant pesticide pressures and so have not had the opportunity to develop resistance as a result of the pesticide pressure when feeding on the recombinant plants. This is particularly true for the corn rootworm larvae as it is highly limited in its ability to move through the soil any great distance from the roots which are more or less adjacent to its local larval environment within the soil. In theory, the adult insects which emerge from the refuge environment will disperse and breed with any insects which emerge from the fields comprising recombinant insecticide-producing corn plants, and if any of the insects which emerge from the recombinant fields have developed a level of resistance to the recombinant insecticidal proteins, the availability of that trait in the subsequent generations will be diluted, reducing or delaying the onset of the emergence of a race which will be totally resistant to the recombinant insecticidal corn plant.

The western corn rootworm, *D. virgifera virgifera*, is a widely distributed pest of corn in North America, and in many instance, chemical insecticides are indiscriminately used to keep the numbers of rootworms below economically damaging levels. In order to assist in the reduction of chemical insecticides used in treatments to control the rootworm populations in crop fields, transgenic lines of corn have been developed which produce a one of a number of amino acid sequence variants of an insecticidal protein produced naturally in the bacterium *Bacillus thuringiensis*. This protein, generally referred to as Cry3Bb, has recently been modified (e.g. U.S. Pat. No. 6,023,013 and related patents and applications; and Vaughn et al., 2005), to contain one or more amino acid sequence variations which, when tested in insect bioassay against the corn rootworm, demonstrates a from about seven (7) to about ten (10) times increase in insecticidal activity when compared to the wild type amino acid sequence. In particular, the enhanced expression of a gene encoding this particular protein in root tissue in corn provides for improved corn rootworm control without the requirement for additional costs of goods by the farmer. In effect, a farmer planting corn rootworm protected corn seeds would not have the costs of labor and of chemical applications in treating fields of corn crops to protect the fields from corn rootworm infestation.

As indicated above, one concern is that a race of rootworm will emerge which has developed resistance to the Cry3Bb protein produced in the corn plants.

One strategy for combating the development of resistance is to select a recombinant corn event which expresses high levels of the insecticidal protein such that one or a few bites of a corn root would cause at least total cessation of feeding and subsequent death of the corn rootworm.

Another strategy would be to combine a second corn rootworm specific insecticidal protein in the form of a recombinant event in the same plant. Preferably the second toxin or toxin complex would have a different mode of action from the Cry3Bb, and preferably, if receptors were involved in the toxicity of the insect to the recombinant protein, the receptors for each of the two or more insecticidal proteins in the same plant would be different so that if a change of function of a receptor or a loss of function of a receptor developed as the cause of resistance to the particular insecticidal protein, then it should not and likely would not affect the insecticidal activity of the remaining toxin which would be shown to bind to a receptor different from the receptor causing the loss of function of one of the two insecticidal proteins cloned into a plant.

Still another strategy would combine a chemical pesticide with a pesticidal protein expressed in a transgenic plant. This could conceivably take the form of a chemical seed treatment of a recombinant seed which would allow for the dispersal into a zone around the root of a pesticidally controlling amount of a chemical pesticide which would protect root tissues from target pest infestation so long as the chemical persisted or the root tissue remained within the zone of pesticide dispersed into the soil. So long as root tissue was within the zone of chemical pesticide protection, a target pest such as a corn rootworm would have to develop resistance to both forms of plant protection, i.e., to the chemical and to the recombinant protein, in the same generation in order to develop resistance to the combination of pesticidal agents. Development of resistance under this particular scenario is believed to be highly unlikely, and in fact, virtually impossible. Only root tissue which would grow beyond the zone of dispersal of the chemical pesticide treatment would be subject to only one form of protection. The seed treatment could take the form of infusion of chemicals or other compositions into the seed, a coating of a composition containing various reagents and agents onto the surface of the seed, or a capsule that encases the seed and which contains within it or embedded into the composition of the capsule a composition containing one or more various reagents and agents, chemicals, and the like which are desired for any number of agriculturally desirable function.

In present conventional agricultural practice, in cases where corn follows corn, it is normal for an insecticide to be applied to protect the corn root system from severe feeding by rootworm larvae. Conventional practice is to treat for the adult beetles or to treat for the larvae. Examples of conventional treatment formulations for adult beetles include the application of carbaryl insecticides (e.g., SEVIN® 80 S at 1.0-2.0 lbs active/acre); fenvalerate or esfenvalerate (e.g., PYDRIN® 2.4 EC at 0.1 to 0.2 lbs active/acre, or ASANA® 0.66 EC at 0.03 to 0.05 lbs active/acre); malathion (57% E at 0.9 lbs active/acre); permethrin (e.g., AMBUSH® 2.0 EC at 0.1 to 0.2 lbs active/acre, or POUNCE® 3.2 EC at 0.1 to 0.2 lbs active ingredient/acre); or PENNCAP-M® at 0.25-0.5 lbs active/acre.

To treat for CRW larvae, conventional practice is to apply a soil insecticide either at or after planting, but preferably as close to egg hatching as possible. Conventional treatments include carbofuran insecticides (e.g., FURADAN® 15 G at 8 oz/1000 ft of row); chloropyrifos (e.g., LORSBAN® 15 G at 8 oz/1000 ft of row); fonophos (e.g., DYFONATE® 20 G at 4.5 to 6.0 oz/1000 ft of row); phorate (e.g., THIMET® 20 G at 6 oz/1000 ft of row); terbufos (e.g., COUNTER® 15 G at 8 oz/1000 ft of row); or tefluthrin (e.g., FORCE® 3 G at 4 to 5 oz/1000 ft of row).

Many of the chemical pesticides listed above are known to be harmful to humans and to animals in general. The environmental harm that these pesticides cause is often exacerbated due to the practice of applying the pesticides by foliar spraying or direct application to the surface of the soil. Wind-drift, leaching, and runoff can cause the migration of a large fraction of the pesticide out of the desired zone of activity and into surface waters and direct contact with birds, animals and humans.

Because of concern about the impact of chemical pesticides on public health and the health of the environment, significant efforts have been made to find ways to reduce the amount of chemical pesticides that are used. Recently, much of this effort has focused on the development of transgenic crops that are engineered to express insect toxicants derived from microorganisms. For example, U.S. Pat. No. 5,877,012 to Estruch et al. discloses the cloning and expression of proteins from such organisms as *Bacillus, Pseudomonas, Clavibacter* and *Rhizobium* into plants to obtain transgenic plants with resistance to such pests as black cutworms, armyworms, several borers and other insect pests. Publication WO/98027218 by Privalle et al. teaches the transformation of monocotyledons, such as corn, with a recombinant DNA sequence encoding peroxidase for the protection of the plant from feeding by corn borers, earworms and cutworms. Jansens et al. (1997), reported the production of transgenic corn containing a gene encoding a crystalline protein from *Bacillus thuringiensis* (Bt) that controlled both generations of the European corn borer. A comprehensive report of field trials of transgenic corn that expresses an insecticidal protein from *B. thuringiensis* has been provided by Armstrong et al. (1995).

It was known that wild-type Bt δ-endotoxins had low activity against coleopteran insects, and Kreig et al., in 1983, reported the first isolation of a coleopteran-toxic *B. thuringiensis* strain. (See U.S. Pat. No. 4,766,203). U.S. Pat. Nos. 4,797,279 and 4,910,016, also disclosed wild-type and hybrid *B. thuringiensis* strains that produced proteins having some coleopteran activity. More recently, however, amino acid sequence variant forms of Cry3Bb have been developed that have significantly higher levels of corn rootworm activity than the activity of the wild type Cry3Bb protein (See, e.g., U.S. Pat. Nos. 6,023,013, 6,060,594, and 6,063,597).

However, it is not known at present whether any transgenic plant expressing a single insecticide directed to controlling corn rootworms will be sufficiently effective to protect corn from damage by corn rootworm in heavily infested fields in which crop rotation on an annual basis is not practiced. In fact, the total control of corn rootworm damage by any one transgenic event may not be desirable in the long term, because of the potential for the development of resistant strains of the target pest.

An alternative to the conventional forms of pesticide or herbicide application is the treatment of plant seeds with compositions that contain pesticides such as insecticides, nematicides, acaricides, fungicides or with organo-phosphate herbicides, and various forms of double stranded RNA's for use in inhibition of plants pest infestation and the like. The use of fungicides or nematicides to protect seeds, and young roots and shoots from attack after planting and sprouting, and the use of low levels of insecticides for the protection of, for example, corn seed from wireworm, has been used for some time. Seed treatment with pesticides has the advantages of providing for the protection of the seeds, while minimizing the amount of pesticide required and limiting the amount of contact with the pesticide and the number of different field applications necessary to attain control of the pests in the field. Seed treatment of herbicide resistant naturally occurring or transgenic varieties with soil stable herbicides that leach into the soil in effective concentrations for controlling the growth and development of weeds and parasitic and saprophytic plants within the rhizosphere of the crop plant are known in the art.

Other examples of the control of pests by applying insecticides directly to plant seed are provided in, for example, U.S. Pat. No. 5,696,144, which discloses that the European corn borer caused less feeding damage to corn plants grown from seed treated with a 1-arylpyrazole compound at a rate of 500 g per quintal of seed than control plants grown from untreated seed. In addition, U.S. Pat. No. 5,876,739 to Turnblad et al. (and its parent, U.S. Pat. No. 5,849,320) disclose a method for controlling soil-borne insects which involves treating seeds with a coating containing one or more polymeric binders and an insecticide. This reference provides a list of insecticides that it identifies as candidates for use in this coating and also names a number of potential target insects. However, while the U.S. Pat. No. 5,876,739 patent states that treating corn seed with a coating containing a particular insecticide protects corn roots from damage by the corn rootworm, it does not indicate or otherwise suggest that such treatment could be used with recombinant seed.

The treatment of recombinant seed with nitroimino- or nitroguanidino-compound pesticides has previously been suggested (See, e.g., WO 99/35913), and insecticides such as thiamethoxam, imidacloprid, thiacloprid, and TI-435 (clothianidin) were identified as being preferred. In the PCT publication, the use of these insecticides was suggested for the seeds of a number of different plant species, and for such seeds having any one of a long list of potential recombinant insecticidal traits. However, that reference provided no guidance as to the details of how such treatments might be effected—such as the amounts of active ingredient that would be necessary per unit amount of seed—and no examples that would give reason to believe that the proposed treatments would actually provide suitable protection.

The deployment of an insect "refuge" is seen as an essential part of insect resistance management (IRM) for Bt transgenic crops. For example, all currently registered transgenic insect protected crops in the United States are required by the Environmental Protection Agency, a federal regulatory agency, to be planted alongside a spatially structured refuge consisting of varieties of the same crop that lack the transgenic insect protection trait. For example, transgenic insect protected corn products containing a single insect resistance trait targeted at controlling lepidopteran pest species grown in the central United States corn belt are required to have at least a 20% corn refuge lacking any insect resistance trait planted alongside or within a relatively near proximity to the transgenic variety. In more southern United States geographical locations, at least a 50% corn refuge lacking any insect resistance trait is required. Similarly, transgenic insect resistant corn products containing a single insect resistance trait targeted at controlling corn rootworm must have at least a 20% corn refuge lacking any insect resistance trait. Insect pressures are higher in the corn refuges lacking insect protection traits and so are not commercially as productive as the insect protected areas of the crop field. The refuge areas of the crop fields produce lower yields of crops than the insect protected areas of the crop fields. Farmers may then be tempted to avoid complying with the refuge requirements because of the perceived cost in yield loss. Widespread non-compliance by farmers would significantly increase the risk of resistance evolution and product failure.

The use of seed mixtures for insect resistance management purposes has been studied previously. For instance, Agi et al. (2001) utilized transgenic cotton plants, comprising a single Bt toxin gene, as the non-refuge plants in studying the efficacy of cotton seed mixtures for yield, crop manangement, and insect resistance management purposes. However it has been widely accepted that studies such as this one demonstrated that use of seed mixtures would not be adequate to meet resistance management requirements for lepidopteran pests because of the degree of larval movement. Mallet & Porter (1992) describe mathematical modeling to study the development of insect populations resistant to Bt toxin in a seed mixture, showing the importance of larval movement. Bates et al. (2005) describe strategies to avoid the buildup of pest populations resistant to a given Bt toxin. Li et al. (2006) reported laboratory experiments on the development of cabbage looper (*Trichoplusia ni*) that were allowed to feed on leaves of transgenic BOLLGARD II or non-transgenic cotton. Ramachandran et al. (2000) evaluated the resistance to diamondback moth of canola grown from seed mixtures that include transgenic seed expressing Cry1Ac. Tabashnik (1994) describes use of seed mixtures in relation to insect resistance management.

Therefore, although recent developments in genetic engineering of plants have improved the ability to protect plants from pests such as insect, fungal, acaricidal, and nematicidal infestation or from pests such as weeds and parasitic and saprophytic plants, without using chemical pesticides, and while such techniques as the treatment of seeds with pesticides and herbicides have reduced the harmful effects of pesticides and herbicides on the environment, numerous problems remain that limit the successful application of these methods under actual field conditions. Accordingly, improved method are needed for the protection of plants, especially corn plants, from feeding damage or other detrimental effects caused by pests. It would be particularly useful if such methods could reduce the required application rate of conventional chemical pesticides and herbicides, and limit the number of separate field operations required for crop planting and cultivation.

In addition, it would be useful to have a method of deploying a non-transgenic or transgenic refuge into a field of transgenic crops instead of peripheral to a field of transgenic crops according to the practice presently required by regulatory agencies.

SUMMARY OF THE INVENTION

In one aspect, the invention comprises a method for deploying a refuge crop in a field of transgenic pest resistant crops comprising the steps of: a) blending transgenic pest resistant crop seeds comprising at least a first transgene conferring resistance to at least a first pest with refuge crop seeds; b) ensuring a uniform mixture of transgenic and refuge crop seeds is provided; and c) planting said mixture in a field, wherein the mixture consists of from between about 100% and about 50% transgenic pest resistant crop seed. In one embodiment, the refuge crop seeds are non-transgenic. In certain embodiments, the refuge crop seeds are transgenic crop seeds comprising a second transgene, wherein the second transgene confers pest resistance to a different pest and/or by a different mode of action relative to the first transgene. The refuge crop seeds as well as the pest resistant crop seeds may also comprise one or more other transgenes conferring another trait. The seed may for instance be selected from the group consisting of corn, cotton, soybean, rice, wheat, sorghum, vegetable, and canola seed.

The first transgene and second transgene may confer resistance to different pests, selected from among lepidopteran pests and a coleopteran pests. For instance, in one embodiment, the first transgene and second transgene encode different *Bacillus thuringiensis* insecticidal δ-endotoxin proteins conferring pest resistance by a different mode of action. The first transgene may confer pest resistance by encoding an insecticidal protein selected from the group consisting of: a recombinant acyl lipid hydrolase protein; a *Bacillus sphaericus* insecticidal protein; a *Bacillus laterosporus* insecticidal protein; an insecticidal protein derived from a *Xenorhabdus* bacteria species; an insecticidal protein derived from a *Photorhabdus* bacteria species; and a *Bacillus thuringiensis* insecticidal δ-endotoxin protein or vegetative insecticidal protein (VIP).

In certain embodiments, the *Bacillus thuringiensis* insecticidal δ-endotoxin protein or vegetative insecticidal protein may be selected from the group consisting of a Cry1 protein or insecticidal variant; a Cry2 protein or insecticidal variant; a Cry3 protein or insecticidal variant; a Cry5 protein or insecticidal variant; a Cry9 protein or insecticidal variant; a chimera of a Cry1, Cry2, Cry3, Cry5, or Cry9 protein; a tIC851 protein; a CryET29 protein; a CryET37 protein; a TIC810 protein; a TIC812 protein; a CryET70 protein; a Cry22 protein; a binary insecticidal protein CryET33 and CryET34; a binary insecticidal protein CryET80 and CryET76; a binary insecticidal protein tIC100 and tIC101; a binary insecticidal protein PS149B1; and a vegetative insecticidal protein (VIP). In particular embodiments, the *Bacillus thuringiensis* insecticidal δ-endotoxin protein or vegetative insecticidal protein may be selected from the group consisting of: Cry1Ab; Cry1Ac; Cry1A.105; Cry1C; Cry1F; Cry1J; Cry2Ab; Cry2Ab2; Cry3A; Cry3Bb; Cry3Bb.11231; Cry3Bb.11098; and VIP3A.

In other embodiments, the transgenic pest resistant crop seeds and/or refuge crop seeds may be treated with a pesticidal agent selected from the group consisting of: a dsRNA targeting suppression of an essential gene of a target pest, an insecticide, acaricide, nematicide, fungicide, and bactericide. The refuge crop seeds may also comprise a transgene that confers a trait selected from the group consisting of herbicide tolerance, insecticidal activity, nematicidal activity, fungicidal activity, bactericidal activity, and acaricidal activity. For instance, the herbicide tolerance transgene may confer tolerance to glyphosate, glufosinate, dicamba, isoxaflutole, a Protoporphyrinogen oxidase inhibitor, or a sulfonylurea herbicide, and the transgenic pest resistant crop seeds and refuge crop seeds may be defined as comprising one or more of the same transgenic or non-transgenic herbicide tolerance traits, for instance the transgenic pest resistant crop seeds and refuge crop seeds may be defined as comprising tolerance to a herbicide selected from the group consisting of glyphosate, glufosinate, dicamba, isoxaflutole, a Protoporphyrinogen oxidase inhibitor, or a sulfonylurea herbicide.

In particular embodiments, the transgenic pest resistant crop seeds may comprise at least two transgenes each conferring pest resistance to the same pest. For instance, the two transgenes may confer pest resistance by different modes of action. In certain embodiments, the mixture may contain at least 80% transgenic pest resistant crop seeds. In alternative embodiments, the mixture contains at least 90% transgenic pest resistant crop seeds.

The transgenic pest resistant crop seeds and refuge crop seeds may further be of a uniform shape and/or size, and may be indistinguishable based for instance on shape, size, or color. Alternatively, they may be distinguishable. In certain embodiments the transgenic pest resistant crop seeds and/or refuge crop seeds may be treated with a seed coating to produce the uniform seed shape and/or size.

In certain embodiments, the transgenic pest resistant crop seeds and/or refuge crop seeds are defined as comprising at least a second transgene that is different from the first transgene, and wherein said second transgene confers resistance to at least a second pest that is different from the first pest. In particular embodiments, the transgenic pest resistant crop seeds and/or refuge crop seeds may comprise a third transgene that encodes a coleopteran endotoxin selected from the group consisting of a Cry3 protein, and CryET33 and CryET34. The third transgene may alternatively encode one or more dsRNAs targeting suppression of one or more essential genes in one or both pests, or a lepidoperan endotoxin selected from the group consisting of: a Cry1 protein; a Cry2 protein; and a VIP.

Further, the transgenic pest resistant crop seeds and/or refuge crop seeds may be defined as comprising at least a second transgene that is different from the first transgene, and wherein said second transgene confers resistance to said first pest with a different mode of action compared to said first transgene. Thus, the refuge crop may comprise at least two different transgenic varieties of the same crop species, wherein a first transgenic variety exhibits resistance to one or more lepidopteran species and is a refuge crop for a second transgenic variety that is different from the first transgenic variety, and said second transgenic variety exhibits resistance to one or more pest species other than lepidopteran species and is a refuge crop for said first transgenic variety. In other embodiments, the refuge crop seeds may further be defined as comprising a transgene conferring production of a pest attractant, such as an insect pheromone.

In another aspect, the invention comprises a method for enhancing the yield of a crop, wherein the yield of a crop produced by planting said mixture in said field is defined as at least equal to the crop yield derived from a crop of an equivalent number and proportion of the first transgenic crop seed and the refuge seed grown under the same conditions but planted in a spatially structured manner. In certain embodiments, the yield of a crop produced by planting said mixture in said field is at least 5%, at least 10%, at least 15%, or at least 25% greater than the crop yield derived from a crop of an equivalent number and proportion of the first transgenic crop seed and the refuge seed grown under the same conditions but planted in a spatially structured manner In yet another aspect, the invention comprises a seed mix produced by a method comprising the steps of: a) blending transgenic pest resistant crop seeds comprising at least a first transgene conferring pest resistance with refuge crop seeds; and b) ensuring a uniform mixture of transgenic and refuge crop seeds is provided, wherein said mixture consists of from about 100% to about 50% transgenic pest resistant crop seed.

DETAILED DESCRIPTION OF THE INVENTION

As used herein, the term "corn" means *Zea mays* or maize and includes all plant varieties that can be bred with corn, including wild maize species.

As used herein, the term "comprising" means "including but not limited to".

As used herein, the terms pest, pesticide, and pesticidal are meant to be interchangeable and inclusive of the following terms: for example, insect, insecticide, and insecticidal when referring to an insect pest; or with the terms, for example, nematode, nematicide, and nematicidal when referring to a nematode pest; or with acaric, acaricide, and acaricidal when referring to an acaric pest; or with fungus or fungal, fungicide, and fungicidal or equivalent terms such as mycotic, and mycocidal when referring to fungal or related pests; or with plant or herb, planticide or herbicide, or planticidal or herbicidal when referring to a plant or a herb pest or growth and development of weeds and parasitic and saprophytic plants within the rhizosphere of the crop plant.

As used herein, the term "transgenic refuge" refers to the requirement of a resistance management plan for reducing or eliminating the likelihood of development of resistance to one or more recombinant traits, such as an insecticide, that is/are either present within a recombinant plant or present adjacent to one or more parts or tissues of a plant. A refuge may or may not be transgenic, however. Refuge seeds are seeds of one or more plant varieties that may be grown into plants that act as a refuge for pests that either feed directly on a particular crop species, or other pests, the presence of which within the local proximity of a particular crop species, results in the damage, decrease in viability, infertility, or decrease in yield of a crop produced from such crop species.

In accordance with the present invention, it has been discovered that corn plants, and by analogy any other plant, can be protected against feeding damage by one or more pests by a method that includes providing a transgenic corn seed encoding an insecticidal protein that has activity against at least one of the pests and then treating the transgenic corn seed with an effective amount of a pesticide. For example, it has been found that the combination of a transgenic corn seed exhibiting bioactivity against corn rootworm as a result of the production of an insecticidal amount of an insecticidal protein within the cells of the corn seed and treatment of the seed with certain chemical or protein pesticides provides unexpectedly synergistic advantages to seeds having such treatment, including unexpectedly superior efficacy for protection against damage to the resulting corn plant by corn rootworm. In particular, it is shown herein that transgenic corn seeds exhibiting bioactivity against corn rootworms as a result of the production of an amino acid variant of a Cry3Bb δ-endotoxin exhibiting improved insecticidal activity compared to the native Cry3Bb protein, in combination with the treatment of such seeds with imidacloprid, was unexpectedly superior to either the transgenic event alone, or to treatment with imidacloprid alone, in protecting resulting corn plants against more severe levels of damage by corn rootworm—levels of damage that are known to reduce corn yield.

Corn plants and seeds that have been engineered to include exogenous genes derived from *Bacillus thuringiensis* that encode for the expression of Cry3 δ-endotoxins having activity against Coleopteran pests are known, as are methods for the treatment of seeds (even some transgenic seeds) with pesticides. Such useful Cry3 proteins include but are not limited to Cry3A proteins, Cry3B proteins, and Cry3C proteins. In addition, other insecticidal proteins are specifically contemplated to be effective in the compositions and methods of the present invention. For example, recombinant forms of acyl lipid hydrolases known as patatins are effective as insecticidal agents (WO 01/49834); and tIC851, CryET70, CryET29, and Cry22 are effective in controlling corn rootworms (U.S. application Ser. No. 09/853,533 filed May 11, 2001). Also, the binary toxins CryET33 and CryET34 (WO 98/13498), tIC100 and tIC101 (U.S. Provisional Application Ser. No. 60/232,099 filed Sep. 12, 2000), CryET80 and CryET76 (WO 00/66742), and PS149B1 (Moellenbeck et al., 2001) have all demonstrated corn rootworm controlling activity. However, it had not been realized until the present invention that certain effective amounts of certain chemical or protein pesticides could be used to treat recombinant corn seeds expressing an insecticidal protein, with the result that the combination would be unexpectedly superior in increasing the efficacy of both the pesticide and the transgene, and would provide the additional advantages of increasing the ability to match pesticidal activity against pest pressure, decreasing cost of treatment and/or application, increasing safety of seed handling, and decreasing environmental impact of either or both the event and the pesticide.

In particular, it has been found that the treatment of transgenic corn seeds that are capable of expressing certain modified Cry3Bb proteins with from about 100 gm to about 400 gm of certain pesticides per 100 kg of seed provided unexpectedly superior protection against corn rootworm. In addition, it is believed that such combinations are also effective to protect the emergent corn plants against damage by black cutworm. The seeds of the present invention are also believed to have the property of decreasing the cost of pesticide use, because less of the pesticide can be used to obtain a required amount of protection than if the innovative method is not used. Moreover, because less pesticide is used and because it is applied prior to planting and without a separate field application, it is believed that the subject method is therefore safer to the operator and to the environment, and is potentially less expensive than conventional methods.

When it is said that some effects are "synergistic", it is meant to include the synergistic effects of the combination on the pesticidal activity (or efficacy) of the combination of the transgenic event and the pesticide. However, it is not intended that such synergistic effects be limited to the pesticidal activity, but that they should also include such unexpected advantages as increased scope of activity, advantageous activity profile as related to type and amount of damage reduction, decreased cost of pesticide and application, decreased pesticide distribution in the environment, decreased pesticide exposure of personnel who produce, handle and plant corn seeds, and other advantages known to those skilled in the art.

The present invention also provides an advantage of increasing the ability to match pesticidal activity against pest pressure. This refers to the ability to design the combination of the transgenic event and the pesticide treatment so that the seed or the resulting plant is provided with effective pesticidal activity during the period when feeding pressure from the target pest on the seed or plant reaches its maximum. By way of example, when a pesticide such as imidacloprid or tefluthrin is applied to a corn seed having a corn rootworm transgenic event, the pesticide can be applied in a coating designed to provide controlled release of the pesticide. The release rate can be selected so that the pesticide provides protection against such other pests as, for example, black cutworm, at the post emergence stage of corn, while the transgenic event provides corn rootworm protection at a later stage of plant development—when such protection is needed.

As used herein, the terms "pesticidal effect" and "pesticidal activity", or "activity" refer to a toxic effect against a pest. The terms "activity against (one or more) pests", also have the same meaning. When it is said that a seed or plant is "protected against feeding damage by one or more pests", it is meant that such seed or plant possesses a feature having direct or indirect action on one or more pests that results in reduced feeding damage by such pest or pests on the seeds, roots, shoots and foliage of plants having such feature as compared to the feeding damage caused under the same conditions to plants not having such feature. Such direct or indirect actions include inducing death of the pest, repelling the pest from the plant seeds, roots, shoots and/or foliage, inhibiting feeding of the pest on, or the laying of its eggs on, the plant seeds, roots, shoots and/or foliage, and inhibiting or preventing reproduction of the pest.

The term "insecticidal activity" has the same meaning as pesticidal activity, except it is limited to those instances where the pest is an insect. Except where specifically noted, when the term "pesticide" is used herein, that term refers to a chemical pesticide that is supplied externally to the seed, and it is not meant to include active agents that are produced by the particular seed or the plant that grows from the particular seed. However, the terms "pesticidal activity" and "insecticidal activity" can be used with reference to the activity of either, or both, an externally supplied pesticide and/or an agent that is produced by the seed or the plant.

One feature of the present invention is a seed of a transgenic corn plant. As used herein, the terms "transgenic corn plant" mean a corn plant or progeny thereof derived from a transformed corn plant cell or protoplast, wherein the plant DNA contains an introduced exogenous DNA molecule not originally present in a native, non-transgenic plant of the same strain.

It is preferred that the seed contains a gene derived from an exogenous source, such as a strain of Bacillus thuringiensis, and in particular, it is preferred that the exogenous gene is one that encodes an insecticidal δ-endotoxin derived from B. thuringiensis. Such δ-endotoxins are described in WO 99/31248, and include the Cry3 toxins. It is preferred that the δ-endotoxins of the present invention include the Cry3B proteins, and even more preferred that the δ-endotoxins include the coleopteran-active Cry3Bb proteins. However, as indicated herein, other insecticidal proteins have been shown to be effective, including but not limited to Cry3A, tIC851, CryET70, Cry22, binary insecticidal proteins CryET33 and CryET34, CryET80 and CryET76, tIC100 and tIC101, and PS149B1, as well as insecticidal proteins derived from Xenorhabdus and Photorhabdus bacteria species, Bacillus laterosporus species, and Bacillus sphaericus species. The nomenclature of the B. thuringiensis insecticidal crystal proteins was set forth by Hone and Whitely, 1989. This nomenclature has been revised, and the revised nomenclature can be found at Dr. Neil Crickmore's website at the University of Sussex in the United Kingdom at epunix.boils.susx.ac.uk/home/neil-crickmore/bt/index.html. The revised nomenclature will be used herein to describe transgenic event features and the δ-endotoxin proteins encoded by the transgenic event. The seed may also contain a transgene encoding an insecticidal agent comprising one or more dsRNA molecules targeting suppression of an essential gene in one or more target pests.

When the term "transgenic event" is used herein, the term is meant to refer to the genetically engineered DNA that is described above, but also to include the protein(s) encoded by the modified gene. A transgenic event in a corn seed, or corn plant, therefore, includes the ability to express a protein. When it is said that a "transgenic event has activity against a pest", it is to be understood that it is the protein that is encoded by the gene that actually has such activity when the protein is expressed and brought into contact with the pest.

The term "transgenic event" is also meant herein to include recombinant plants produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr (1987).

WO 99/31248 describes methods for genetically engineering *B. thuringiensis* δ-endotoxin genes so that modified δ-endotoxins can be expressed. The modified δ-endotoxins differ from the wild-type proteins by having specific amino acid substitutions, additions or deletions as compared with the proteins produced by the wild-type organism. Such modified δ-endotoxins are identified herein by the use of an asterisk (*), or by reference to a specific protein by its identifying number. Thus, a genetically modified Cry3 δ-endotoxin would be expressed as Cry3*, one of which is, for example, Cry3Bb.11231.

Some of the modified δ-endotoxins that are described in WO 99/31248 were found to have enhanced activity against coleopteran insects, and in particular against *Diabrotica* spp., including corn rootworm. As used herein, the term "enhanced activity" refers to the increased insecticidal activity of a modified toxin as compared with the activity of the same toxin without the amino acid modifications when both are tested under the same conditions. In particular, it was found that Cry3* δ-endotoxins exhibited enhanced activity against corn rootworm, and are therefore preferred for use in the present invention. More preferred are Cry3B* δ-endotoxins, and even more preferred are Cry3Bb* δ-endotoxins. Even more preferred transgenic events are those that comprise the ability to express modified δ-endotoxins Cry3Bb.11231 (which was deposited on May 27, 1997 as NRRL Accession Number B-21769) and Cry3Bb.11098 (which was deposited on Nov. 28, 1997 as NRRL Accession Number B-21093). Amino acid sequences for these two preferred proteins are given in WO 99/31248, as are the nucleotide sequences that encode them. Transgenic plants known as transgenic events herein derived from the insertion of a DNA sequence designed to express the Cry3Bb variant protein 11231 were designated as transgenic event No. MON853. Transgenic plants known as transgenic events herein derived from the insertion of a DNA sequence designed to express the Cry3Bb variant protein 11098 were designated as transgenic event No. MON863. Similarly, other transgenic events have been obtained including MON89034, and MON88017, among others.

It has also been found that a preferred use of the present invention is for reducing pest feeding damage when used in combination with seeds having transgenic events that have certain levels of effectiveness against such pest. To illustrate beneficial levels of effectiveness, the following example will use the Iowa Root Rating Method (Hills and Peters, 1971), which measures corn rootworm feeding damage to corn roots on a 1-6 scale. In the rating, 1=no damage or only a few minor feeding scars; 2=feeding scars evident but no roots eaten off to within 1½ inch of the plant; 3=several roots eaten off to within 1½ inch of the plant, but never the equivalent of an entire node of roots is destroyed; 4=one root node completely destroyed; 5=two root nodes completely destroyed; and 6=three or more root nodes destroyed. A destroyed root is defined as a root that has been pruned to within 1½ inch of the base. Pruned roots do not have to originate from a single node, but all pruned roots must equal the equivalent of a full node to count as a destroyed node.

As used herein, a transgenic event is within a preferred range of effectiveness level against a target pest if that event reduces feeding damage by that pest by a certain amount as compared with the same crop without the transgenic event, but does not prevent substantially all damage by the target pest. For example, if 10% of transgenic corn suffered corn rootworm damage of 4 or higher on the Iowa 1-6 Scale, while 80% of non-transgenic corn suffered damage of 4 or higher, then it could be said that the damage to the transgenic corn was (10/80)×100=12.5% of that of the non-transgenic corn. For the purposes of the present invention, it will be understood that a transgenic event in corn is within a preferred range of effectiveness level if corn having such event suffers from about 5% to about 50% of the damage suffered by non-transgenic corn due to the same pest under the same conditions. It is more preferred that corn having such transgenic event suffers from about 10% to about 40% of the damage suffered by non-transgenic corn by the same pest under the same conditions, even more preferred is damage of from about 15% to about 30%, and yet more preferred is damage of from about 20% to about 30% of the damage suffered by non-transgenic corn by the same pest under the same conditions. As used herein, when the term "about" is used to describe the degree of damage to corn, it is to be understood that the degree of damage can be above or below the limits described by as much as 1% or 2% and still be considered to be within the ranges described. By way of example, a level of 4.5% damage would be regarded as being "about 5%".

Without wishing to be bound to this or any other theory, it is believed that pesticidal seed treatment can provide significant advantages when combined with a transgenic event that provides protection that is within the examples of preferred effectiveness ranges against a target pest. In addition, it is believed that there are situations that are well known to those having skill in the art, where it is advantageous to have such transgenic events within the preferred range of effectiveness.

The present invention also includes seeds and plants having more than one transgenic event. Such combinations are referred to as "stacked" transgenic events. These stacked transgenic events can be events that are directed at the same target pest, or they can be directed at different target pests. In one method, a seed having the ability to express a Cry 3 protein also has the ability to express at least one other insecticidal protein that is different from a Cry 3 protein.

In another method, the seed having the ability to express a Cry 3 protein also has a transgenic event that provides herbicide tolerance. It may be preferred that the transgenic event that provides herbicide tolerance is an event that provides resistance to glyphosate, N-(phosphonomethyl) glycine, including the isopropylamine salt form of such herbicide, even more preferred is the transgenic event that is effective to provide the herbicide resistance of ROUNDUP READY® plants and seeds available from Monsanto Co., St. Louis, Mo. In the present method, a corn seed having a transgenic event may be treated with a pesticide.

Pesticides suitable for use in the invention include pyrethrins and synthetic pyrethroids; oxadizine derivatives; chloronicotinyls; nitroguanidine derivatives; triazoles; organophosphates; pyrrols; pyrazoles; phenyl pyrazoles; diacylhydrazines; biological/fermentation products; and carbamates. Known pesticides within these categories are listed in *The Pesticide Manual* (1997).

Pyrethroids that are useful in the present composition include pyrethrins and synthetic pyrethroids. The pyrethrins that are preferred for use in the present method include, without limitation, 2-allyl-4-hydroxy-3-methyl-2-cyclopenten-1-one ester of 2,2-dimethyl-3-(2methyl propenyl)-cyclopropane carboxylic acid, and/or (2-methyl-1-propenyl)-2-methoxy-4-oxo-3-(2 propenyl)-2-cyclopenten-1-yl ester and mixtures of cis and trans isomers thereof (Chemical Abstracts Service Registry Number ("CAS RN") 8003-34-7).

Synthetic pyrethroids that are preferred for use in the present invention include (s)-cyano(3-phenoxyphenyl) methyl 4-chloro alpha (1-methylethyl)benzeneacetate (fenvalerate, CAS RN 51630-58-1), (S)-cyano (3-phenoxyphenyl) methyl (S)-4-chloro-alpha-(1-methylethyl) benzeneacetate (esfenvalerate, CAS RN 66230-04-4), (3-phenoxyphenyl)-methyl(+)cis-trans-3-(2,2-dichoroethenyl)-2,2-dimethylcyclopropanecarboxylate (permethrin, CAS RN 52645-53-1), (±) alpha-cyano-(3-phenoxyphenyl) methyl(+)-cis,trans-3-(2,2-dichloroethenyl)-2,2-dimethylcyclopropane carboxylate (cypermethrin, CAS RN 52315-07-8), (beta-cypermethrin, CAS RN 65731-84-2), (theta cypermethrin, CAS RN 71697-59-1), S-cyano (3-phenoxyphenyl) methyl (±) cis/trans 3-(2,2-dichloroethenyl) 2,2 dimethylcyclopropane carboxylate (zeta-cypermethrin, CAS RN 52315-07-8), (s)-alpha-cyano-3-phenoxybenzyl (IR,3R)-3-(2,2-dibromovinyl)-2,2-dimethyl cyclopropanecarboxylate (deltamethrin, CAS RN 52918-63-5), alpha-cyano-3-phenoxybenzyl 2,2,3,3,-tetramethyl cyclopropoanecarboxylate (fenpropathrin, CAS RN 64257-84-7), (RS)-alpha-cyano-3-phenoxybenzyl(R)-2-[2-chloro-4-(trifluoromethyl)anilino]-3-methylbutanoate (tau-fluvalinate, CAS RN 102851-06-9), (2,3,5,6-tetrafluoro-4-methylphenyl)-methyl-(1 alpha, 3 alpha)-(Z)-(±)-3-(2-chloro-3,3,3-trifluoro-1-propenyl)-2,2-dimethylcyclopropanecarboxylate (tefluthrin, CAS RN 79538-32-2), (±)-cyano (3-phenoxyphenyl) methyl (±)-4-(difluoromethoxy)-alpha-(1-methyl ethyl) benzeneacetate (flucythrinate, CAS RN 70124-77-5), cyano(4-fluoro-3-phenoxyphenyl)methyl 3-[2-chloro-2-(4-chlorophenyl)ethenyl]-2,2-dimethylcyclopropanecarboxylate (flumethrin, CAS RN 69770-45-2), cyano(4-fluoro-3-phenoxyphenyl) methyl 3-(2,2-dichloroethenyl)-2,2-dimethyl-cyclopropanedarboxylate (cyfluthrin, CAS RN 68359-37-5), (beta cyfluthrin, CAS RN 68359-37-5), (transfluthrin, CAS RN 118712-89-3), (S)-alpha-cyano-3-phenoxybenzyl(Z)-(IR-cis)-2,2-dimethyl-3-[2-(2,2,2-trifluoro-trifluoromethyl-ethoxycarbonyl)vinyl]cyclopropane carboxylate (acrinathrin, CAS RN 101007-06-1), (IR cis) S and (IS cis) R enantiomer isomer pair of alpha-cyano-3-phenoxybenzyl-3-(2,2dichlorovinyl)-2,2-dimethylcyclopropane carboxylate (alpha-cypermethrin, CAS RN 67375-30-8), [IR,3S)3 (1'RS)(1',2',2',2'-tetrabromoethyl)]-2,2-dimethyl cyclopropanecarboxylic acid (s)-alpha-cyano-3-phenoxybenzyl ester (tralomethrin, CAS RN 66841-25-6), cyano-(3-phenoxyphenyl) methyl 2,2-dichloro-1-(4-ethoxyphenyl)cyclopropane carboxylate (cycloprothrin, CAS RN 63935-38-6), [la, 3α(Z)]-(±)-cyano-(3-phenoxyphenyl)methyl 3-(2-chloro-3,3,3-trifluoro-1-propenyl)-2,2-cimethylcyclopropanecarboxylate (cyhalothrin, CAS RN 68085-85-8), [1 alpha (s), 3 alpha(z)]-cyano(3-phenoxyphenyl) methyl-3-(2-chloro-3,3,3-trifluoro-1-propenyl)-2,2-dimethylcyclopropane carboxylate (lambda cyhalothrin, CAS RN 91465-08-6), (2-methyl [1,1'-biphenyl]-3-yl) methyl 3-(2-chloro-3,3,3-trifluoro-1-propenyl)-2,2-dimethylcyclopropanecarboxylate (bifenthrin, CAS RN 82657-04-3), 5-1-benzyl-3-furylmethyl-d-cis(1R,3S,E)2,2-dimethyl-3-(2-oxo,-2,2,4,5 tetrahydro thiophenylidenemethyl)cyclopropane carboxylate (kadethrin, RU15525, CAS RN 58769-20-3), [5-(phenyl methyl)-3-furanyl]-3-furanyl 2,2-dimethyl-3-(2-methyl-1-propenyl) cyclopropane carboxylate (resmethrin, CAS RN 10453-86-8), (1R-trans)-[5-(phenylmethyl)-3-furanyl]methyl 2,2-dimethyl-3-(2-methyl-1-propenyl)cyclopropanecarboxylate (bioresmethrin, CAS RN 28434-01-7), 3,4,5,6-tetra hydro phthalimidomethyl-(IRS)-cis-trans-chrysanthemate (tetramethrin, CAS RN 7696-12-0), 3-phenoxybenzyl-d,l-cis,trans 2,2-dimethyl-3-(2-methylpropenyl) cyclopropane carboxylate (phenothrin, CAS RN 26002-80-2); (empenthrin, CAS RN 54406-48-3); (cyphenothrin; CAS RN 39515-40-7), (prallethrin, CAS RN 23031-36-9), (imiprothrin, CAS RN 72963-72-5), (RS)-3-allyl-2-methyl-4-oxcyclopent-2-enyl-(1A,3R; 1R,3S)-2,2-dimethyl-3-(2-methylprop-1-enyl) cyclopropane carboxylate (allethrin, CAS RN 584-79-2), (bioallethrin, CAS RN 584-79-2), and (ZXI8901, CAS RN 160791-64-0). It is believed that mixtures of one or more of the aforementioned synthetic pyrethroids can also be used in the present invention. Particularly preferred synthetic pyrethroids are tefluthrin, lambda cyhalothrin, bifenthrin, permethrin and cyfluthrin. Even more preferred synthetic pyrethroids are tefluthrin and lambda cyhalothrin, and yet more preferred is tefluthrin.

Insecticides that are oxadiazine derivatives are useful in the subject method. The oxadizine derivatives that are preferred for use in the present invention are those that are identified in U.S. Pat. No. 5,852,012. More preferred oxadiazine derivatives are 5-(2-chloropyrid-5-ylmethyl)-3-methyl-4-nitroiminoperhydro-1,3,5-oxadiazine, 5-(2-chlorothiazol-5-ylmethyl)-3-methyl-4-nitroiminoperhydro-1,3, 5-oxadiazine, 3-methyl-4-nitroimino-5-(1-oxido-3-pyridinomethyl)perhydro-1,3,5-oxadiazine, 5-(2-chloro-1-oxido-5-pyridiniomethyl)-3-methyl-4-nitroiminoperhydro-1,3,5-oxidiazine; and 3-methyl-5-(2-methylpyrid-5-ylmethyl)-4-nitroiminoperhydro-1,3,5-oxadiazine. Even more preferred is thiamethoxam (CAS RN 153719-23-4).

Chloronicotinyl insecticides are also useful in the subject method. Chloronicotinyls that are preferred for use in the subject composition are described in U.S. Pat. No. 5,952,358, and include acetamiprid ((E)-N-[(6-chloro-3-pyridinyl)methyl]-N'-cyano-N-methyleneimidamide, CAS RN 135410-20-7), imidacloprid (1-[(6-chloro-3-pyridinyl) methol]-N-nitro-2-imidazolidinimime, CAS RN 138261-41-3), and nitenpyram (N-[(6-chloro-3-pyridinyl)methyl]-N-ethyl-N'-methyl-2-nitro-1,1-ethenediamine, CAS RN 120738-89-8).

Nitroguanidine insecticides are useful in the present method. Such nitroguanidines can include those described in U.S. Pat. Nos. 5,633,375, 5,034,404 and 5,245,040.

Pyrrols, pyrazoles and phenyl pyrazoles that are useful in the present method include those that are described in U.S. Pat. No. 5,952,358. Preferred pyrazoles include chlorfenapyr (4-bromo-2-(4-chlorophenyl)-1-ethoxymethyl-5-trifluoromethylpyrrole-3-carbonitrile, CAS RN 122453-73-0), fenpyroximate ((E)-1,1-dimethylethyl-4 [[[[(1,3-dimethyl-5-phenoxy-1H-pyrazole-4-yl)methylene]amino] oxy]methyl]benzoate, CAS RN 111812-58-9), and tebufenpyrad (4-chloro-N[[4-1,1-dimethylethyl)phenyl]methyl]-3-ethyl-1-methyl-1H-pyrazole-5-carboxamide, CAS RN 119168-77-3). A preferred phenyl pyrazole is fipronil (5-amino-[2,6-dichloro-4-(trifluoromethyl)phenyl]-4-[(1R,S)-(trifluoromethyl)sulfinyl]-1H-pyrazole-3-carbonitrile, CAS RN 120068-37-3). Diacylhydrazines that are useful in the present invention include halofenozide (4-chlorobenzoate-2-benzoyl-2-(1,1-dimethylethyl)-hydrazide, CAS RN 112226-61-6), methoxyfenozide (RH-2485; N-tert-butyl-N'-(3-methoxy-o-toluoyl)-3,5-xylohydrazide, CAS RN 161050-58-4), and tebufenozide (3,5-dimethylbenzoic acid 1-(1,1-dimethylethyl)-2,(4-ethylbenzoyl)hydrazide, CAS RN 112410-23-8).

Triazoles, such as amitrole (CAS RN 61-82-5) and triazamate are useful in the method of the present invention. A preferred triazole is triazamate (ethyl [[1-[(dimethylamino)

carbonyl]-3-(1,1-dimethylethyl)-1H-1,2,4-triazol-5-yl]thio] acetate, CAS RN 112143-82-5).

Biological/fermentation products, such as avermectin (abamectin, CAS RN 71751-41-2) and spinosad (XDE-105, CAS RN 131929-60-7) are useful in the present method.

Organophosphate insecticides are also useful as one of the components of the present method. Preferred organophophate insecticides include acephate (CAS RN 30560-19-1), chlorpyrifos (CAS RN 2921-88-2), chlorpyrifos-methyl (CAS RN 5598-13-0), diazinon (CAS RN 333-41-5), fenamiphos (CAS RN 22224-92-6), and malathion (CAS RN 121-75-5).

In addition, carbamate insecticides are useful in the subject method. Preferred carbamate insecticides are aldicarb (CAS RN 116-06-3), carbaryl (CAS RN 63-25-2), carbofuran (CAS RN 1563-66-2), oxamyl (CAS RN 23135-22-0) and thiodicarb (CAS RN 59669-26-0).

When an insecticide is described herein, it is to be understood that the description is intended to include salt forms of the insecticide as well as any isomeric and/or tautomeric form of the insecticide that exhibits the same insecticidal activity as the form of the insecticide that is described.

The insecticides that are useful in the present method can be of any grade or purity that pass in the trade as such insecticide. Other materials that accompany the insecticides in commercial preparations as impurities can be tolerated in the subject methods and compositions, as long as such other materials do not destabilize the composition or significantly reduce or destroy the activity of any of the insecticide components or the transgenic event against the target pest(s). One of ordinary skill in the art of the production of insecticides can readily identify those impurities that can be tolerated and those that cannot.

It has been found that the present method is useful to protect seeds and plants against a wide array of agricultural pests, including insects, mites, fungi, yeasts, molds, bacteria, nematodes, weeds, and parasitic and saprophytic plants.

When an insect is the target pest for the present invention, such pests include but are not limited to:

from the order Lepidoptera, for example, *Acleris* spp., *Adoxophyes* spp., *Aegeria* spp., *Agrotis* spp., *Alabama argillaceae*, *Amylois* spp., *Anticarsia gemmatalis*, *Archips* spp, *Argyrotaenia* spp., *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia binotalis*, *Cryptophlebia leucotreta*, *Cydia* spp., *Diatraea* spp. (for instance *Diatraea grandiosella*), *Diparopsis castanea*, *Earias* spp., *Ephestia* spp., *Eucosma* spp., *Eupoecilia ambiguella*, *Euproctis* spp., *Euxoa* spp., *Grapholita* spp., *Hedya nubiferana*, *Helicoverpa* spp. (for instance *H. zea*, *H. punctigera*, or *H. armigera*), *Heliothis* spp., *Hellula undalis*, *Hyphantria cunea*, *Keiferia lycopersicella*, *Leucoptera scitella*, *Lithocollethis* spp., *Lobesia botrana*, *Lymantria* spp., *Lyonetia* spp., *Malacosoma* spp., *Mamestra brassicae*, *Manduca sexta*, *Operophtera* spp., *Ostrinia nubilalis*, *Pammene* spp., *Pandemis* spp., *Panolis flammea*, *Pectinophora gossypiella*, *Phthorimaea operculella*, *Pieris rapae*, *Pieris* spp., *Plutella xylostella*, *Prays* spp., *Richia albicosta*, *Scirpophaga* spp., *Sesamia* spp., *Sparganothis* spp., *Spodoptera* spp. (e.g. *S. frugiperda*), *Synanthedon* spp., *Thaumetopoea* spp., *Tortrix* spp., *Trichoplusia ni* and *Yponomeuta* spp.;

from the order Coleoptera, for example, *Agriotes* spp., *Anthonomus* spp., *Atomaria linearis*, *Chaetocnema tibialis*, *Cosmopolites* spp., *Curculio* spp., *Dermestes* spp., *Diabrotica* spp. (for instance *Diabrotica virgifera virgifera* LeConte, *Diabrotica barberi* Smith and *Diabrotica barberi*, *Diabrotica undecimpunctata howardi*, *Diabrotica speciosa*, and *Diabrotica viridula*), *Epilachna* spp., *Eremnus* spp., *Leptinotarsa decemlineata*, *Lissorhoptrus* spp., *Melolontha* spp., *Oryzaephilus* spp., *Otiorhynchus* spp., *Phlyctinus* spp., *Popillia* spp., *Psylliodes* spp., *Rhizopertha* spp., Scarabeidae, *Sitophilus* spp., *Sitotroga* spp., *Tenebrio* spp., *Tribolium* spp. and *Trogoderma* spp.;

from the order Orthoptera, for example, *Blatta* spp., *Blattella* spp., *Gryllotalpa* spp., *Leucophaea maderae*, *Locusta* spp., *Periplaneta* ssp., and *Schistocerca* spp.;

from the order Isoptera, for example, *Reticulitemes* ssp;

from the order Psocoptera, for example, *Liposcelis* spp.;

from the order Anoplura, for example, *Haematopinus* spp., *Linognathus* spp., *Pediculus* spp., *Pemphigus* spp. and *Phylloxera* spp.;

from the order Mallophaga, for example, *Damalinea* spp. and *Trichodectes* spp.;

from the order Thysanoptera, for example, *Franklinella* spp., *Hercinothrips* spp., *Taeniothrips* spp., *Thrips palmi*, *Thrips tabaci* and *Scirtothrips aurantii*;

from the order Heteroptera, for example, *Cimex* spp., *Distantiella theobroma*, *Dysdercus* spp., *Euchistus* spp., *Eurygaster* spp., *Leptocorisa* spp., *Nezara* spp., *Piesma* spp., *Rhodnius* spp., *Sahlbergella singularis*, *Scotinophara* spp. and *Triatoma* spp.;

from the order Homoptera, for example, *Aleurothrixus floccosus*, *Aleyrodes brassicae*, *Aonidiella* spp., Aphididae, *Aphis* spp., *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma larigerum*, *Erythroneura* spp., *Gascardia* spp., *Laodelphax* spp., *Lacanium corni*, *Lepidosaphes* spp., *Macrosiphus* spp., *Myzus* spp., *Nehotettix* spp., *Nilaparvata* spp., *Paratoria* spp., *Pemphigus* spp., *Planococcus* spp., *Pseudaulacaspis* spp., *Pseudococcus* spp., *Psylla* ssp., *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Trioza erytreae* and *Unaspis citri*;

from the order Hymenoptera, for example, *Acromyrmex*, *Atta* spp., *Cephus* spp., *Diprion* spp., Diprionidae, *Gilpinia polytoma*, *Hoplocampa* spp., *Lasius* sppp., *Monomorium pharaonis*, *Neodiprion* spp, *Solenopsis* spp. and *Vespa* ssp.;

from the order Diptera, for example, *Aedes* spp., *Antherigona soccata*, *Bibio hortulanus*, *Calliphora erythrocephala*, *Ceratitis* spp., *Chrysomyia* spp., *Culex* spp., *Cuterebra* spp., *Dacus* spp., *Drosophila melanogaster*, *Fannia* spp., *Gastrophilus* spp., *Glossina* spp., *Hypoderma* spp., *Hyppobosca* spp., *Liriomysa* spp., *Lucilia* spp., *Melanagromyza* spp., *Musca* ssp., *Oestrus* spp., *Orseolia* spp., *Oscinella fit*, *Pegomyia hyoscyami*, *Phorbia* spp., *Rhagoletis pomonella*, *Sciara* spp., *Stomoxys* spp., *Tabanus* spp., *Tannia* spp. and *Tipula* spp., from the order Siphonaptera, for example, *Ceratophyllus* spp. and *Xenopsylla cheopis*, and from the order Thysanura, for example, *Lepisma saccharina*.

It has been found that the present invention is particularly effective when the insect pest is a *Diabrotica* spp., and especially when the pest is *Diabrotica virgifera*, *Diabrotica barberi*, or *Diabrotica undecimpunctata*.

Another application wherein the present invention is believed to be particularly effective is when the pesticide has activity against a weed or a parasitic or saprophytic plant and the transgenic event has activity against a member selected from the group consisting of *Diabrotica virgifera*, *Diabrotica barberi* and *Diabrotica undecimpunctata*. This is believed to be more preferred useful when the weed or a parasitic or saprophytic plant is the plant known as "Striga" (e.g. Striga spp.; such as Striga asiatica), and even more preferred when the pesticide is ROUNDUP® (available from Monsanto Company).

In the method of the present invention, the pesticide may be applied to a transgenic corn seed. Although it is believed that the present method can be applied to a transgenic corn seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. In one embodiment, for example, the treatment can be applied to seed corn that has been harvested, cleaned and dried to a moisture content below about 15% by weight. In an alternative embodiment, the seed can be one that has been dried and then primed with water and/or another material and then re-dried before or during the treatment with the pesticide. Within the limitations just described, it is believed that the treatment can be applied to the seed at any time between harvest of the seed and sowing of the seed. As used herein, the term "unsown seed" is meant to include seed at any period between the harvest of the seed and the sowing of the seed in the ground for the purpose of germination and growth of the plant.

When it is said that unsown seed is "treated" with the pesticide, such treatment is not meant to include those practices in which the pesticide is applied to the soil, rather than to the seed. For example, such treatments as the application of the pesticide in bands, "T"-bands, or in-furrow, at the same time as the seed is sowed are not considered to be included in the present invention.

The pesticide, or combination of pesticides, can be applied "neat", that is, without any diluting or additional components present. However, the pesticide is typically applied to the seeds in the form of a pesticide formulation. This formulation may contain one or more other desirable components including but not limited to liquid diluents, binders to serve as a matrix for the pesticide, fillers for protecting the seeds during stress conditions, and plasticizers to improve flexibility, adhesion and/or spreadability of the coating. In addition, for oily pesticide formulations containing little or no filler, it may be desirable to add to the formulation drying agents such as calcium carbonate, kaolin or bentonite clay, perlite, diatomaceous earth or any other adsorbent material. Use of such components in seed treatments is known in the art. See, e.g., U.S. Pat. No. 5,876,739. The skilled artisan can readily select desirable components to use in the pesticide formulation depending on the seed type to be treated and the particular pesticide that is selected. In addition, readily available commercial formulations of known pesticides may be used, as demonstrated in the examples below.

The seeds may also be treated with one or more of the following ingredients: other pesticides, including compounds which act only below the ground; fungicides, such as captan, thiram, metalaxyl, (methoxam=resolved isomer of metalaxyl), fludioxonil, oxadixyl, and isomers of each of those materials, and the like; herbicides, including compounds selected from carbamates, thiocarbamates, acet-amides, triazines, dinitroanilines, glycerol ethers, pyridazi-nones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; fertilizers; biocontrol agents such as naturally-occurring or recombinant bacteria and fungi from the genera Rhizobium, Bacillus, Pseudomonas, Serratia, Trichoderma, Glomus, Gliocladium and mycorrhizal fungi; and double stranded or stabilized RNA molecules that, when consumed by a pest or pest cell, act to reduce or eliminate some essential function within the pest or pest cell which further results in one or more of the death, infertility, feeding suppression, stunting, repulsion, or lack of further development and differentiation of the pest or pest cell. These ingredients may be added as a separate layer on the seed or alternatively may be added as part of the pesticide composition.

Preferably, the amount of the novel composition or other ingredients used in the seed treatment should not inhibit generation of the seed, or cause phytotoxic damage to the seed.

The pesticide formulation that is used to treat the transgenic corn seed in the present invention can be in the form of a suspension; emulsion; slurry of particles in an aqueous medium (e.g., water); wettable powder; wettable granules (dry flowable); and dry granules. If formulated as a suspension or slurry, the concentration of the active ingredient in the formulation is preferably about 0.5% to about 99% by weight (w/w), preferably 5-40%.

As mentioned above, other conventional inactive or inert ingredients can be incorporated into the formulation. Such inert ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyr-rolidone/vinyl acetate PVP/VA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like. Further inert ingredients useful in the present invention can be found in McCutcheon's Emulsifiers and Detergents (1996). Additional inert ingredients useful in the present invention can be found in McCutcheon's Functional Materials (1996).

The pesticides and pesticide formulations of the present invention can be applied to seeds by any standard seed treatment methodology, including but not limited to mixing in a container (e.g., a bottle or bag), mechanical application, tumbling, spraying, and immersion. Any conventional active or inert material can be used for contacting seeds with pesticides according to the present invention, such as conventional film-coating materials including but not limited to water-based film coating materials such as Sepiret (Seppic, Inc., Fairfield, N.J.) and Opacoat (Berwind Pharm. Services, Westpoint, Pa.).

The subject pesticides can be applied to a seed as a component of a seed coating. Seed coating methods and compositions that are known in the art are useful when they are modified by the addition of one of the embodiments of the combination of pesticides of the present invention. Such coating methods and apparatus for their application are disclosed in, for example, U.S. Pat. Nos. 5,918,413, 5,891, 246, 5,554,445, 5,389,399, 5,107,787, 5,080,925, 4,759,945 and 4,465,017. Seed coating compositions are disclosed, for example, in U.S. Pat. Nos. 5,939,356, 5,882,713, 5,876,739, 5,849,320, 5,834,447, 5,791,084, 5,661,103, 5,622,003, 5,580,544, 5,328,942, 5,300,127, 4,735,015, 4,634,587, 4,383,391, 4,372,080, 4,339,456, 4,272,417 and 4,245,432, among others. Useful seed coatings may contain one or more binders and at least one of the subject combinations of pesticides.

Binders that are useful in the present invention preferably comprise an adhesive polymer that may be natural or synthetic and is without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

It is preferred that the binder be selected so that it can serve as a matrix for the subject pesticides. While the binders disclosed above may all be useful as a matrix, the specific binder will depend upon the properties of the combination of pesticides. The term "matrix", as used herein, means a continuous solid phase of one or more binder compounds throughout which is distributed as a discontinuous phase one or more of the subject pesticides. Optionally, a filler and/or other components can also be present in the matrix. The term "matrix" is to be understood to include what may be viewed as a matrix system, a reservoir system or a microencapsulated system. In general, a matrix system consists of pesticides of the present invention and filler uniformly dispersed within a polymer, while a reservoir system consists of a separate phase comprising the subject pesticides, that is physically dispersed within a surrounding, rate-limiting, polymeric phase. Microencapsulation includes the coating of small particles or droplets of liquid, but also to dispersions in a solid matrix.

The amount of binder in the coating can vary, but will be in the range of about 0.01 to about 25% of the weight of the seed, more preferably from about 0.05 to about 15%, and even more preferably from about 0.1% to about 10%.

As mentioned above, the matrix can optionally include a filler. The filler can be an absorbent or an inert filler, such as are known in the art, and may include woodflours, clays, activated carbon, sugars, diatomaceous earth, cereal flours, fine-grain inorganic solids, calcium carbonate, and the like. Clays and inorganic solids, which may be used, include calcium bentonite, kaolin, china clay, talc, perlite, mica, vermiculite, silicas, quartz powder, montmorillonite and mixtures thereof. Sugars, which may be useful, include dextrin and maltodextrin. Cereal flours include wheat flour, oat flour and barley flour.

The filler is selected so that it will provide a proper microclimate for the seed, for example the filler is used to increase the loading rate of the active ingredients and to adjust the control-release of the active ingredients. The filler can aid in the production or process of coating the seed. The amount of filler can vary, but generally the weight of the filler components will be in the range of about 0.05 to about 75% of the seed weight, more preferably about 0.1 to about 50%, and even more preferably about 0.5% to 15%.

The pesticides that are useful in the coating are those pesticides that are described herein. The amount of pesticide that is used for the treatment of the seed will vary depending upon the type of seed and the type of active ingredients, but the treatment will comprise contacting the seeds with an amount of the combination of pesticides that is pesticidally effective. When insects are the target pest, that amount will be an amount of the insecticide that is insecticidally effective. As used herein, an insecticidally effective amount means that amount of insecticide that will kill insect pests in the larvae or pupal state of growth, or will consistently reduce or retard the amount of damage produced by insect pests.

In general, the amount of pesticide that is applied to the seed in the treatment will range from about 10 gm to about 2000 gm of the active ingredient of the pesticide per 100 kg of the weight of the seed. Preferably, the amount of pesticide will be within the range of about 50 gm to about 1000 gm active per 100 kg of seed, more preferably within the range of about 100 gm to about 600 gm active per 100 kg of seed, and even more preferably within the range of about 200 gm to about 500 gm of active per 100 kg of seed weight. Alternatively, it has been found to be preferred that the amount of the pesticide be over about 60 gm of the active ingredient of the pesticide per 100 kg of the seed, and more preferably over about 80 gm per 100 kg of seed.

In certain embodiments of the present invention the transgenic event comprises the ability to express a Cry3Bb.11231 protein or a Cry3Bb.11098 protein, and the pesticide is selected from either imidacloprid or tefluthrin.

The pesticides that are used in the treatment must not inhibit germination of the seed and should be efficacious in protecting the seed and/or the plant during that time in the target insect's life cycle in which it causes injury to the seed or plant. In general, the coating will be efficacious for approximately 0 to 120 days after sowing.

The pesticides of the subject invention can be applied to the seed in the form of a coating. The use of a coating is particularly effective in accommodating high pesticidal loads, as can be required to treat typically refractory pests, such as corn rootworm, while at the same time preventing unacceptable phytotoxicity due to the increased pesticidal load.

Optionally, a plasticizer can be used in the coating formulation. Plasticizers are typically used to make the film that is formed by the coating layer more flexible, to improve adhesion and spreadability, and to improve the speed of processing. Improved film flexibility is important to minimize chipping, breakage or flaking during storage, handling or sowing processes. Many plasticizers may be used, however, useful plasticizers include polyethylene glycol, glycerol, butylbenzylphthalate, glycol benzoates and related compounds. The range of plasticizer in the coating layer will be in the range of from bout 0.1 to about 20% by weight.

When the pesticide used in the coating is an oily type formulation and little or no filler is present, it may be useful to hasten the drying process by drying the formulation. This optional step may be accomplished by means will known in the art and can include the addition of calcium carbonate, kaolin or bentonite clay, perlite, diatomaceous earth, or any absorbent material that is added preferably concurrently with the pesticidal coating layer to absorb the oil or excess moisture. The amount of calcium carbonate or related compounds necessary to effectively provide a dry coating will be in the range of about 0.5 to about 10% of the weight of the seed.

The coatings formed with the pesticide are preferably of the type that are capable of effecting a slow rate of release of the pesticide by diffusion or movement through the matrix to the surrounding medium.

In addition to the coating layer, the seed may be treated with one or more of the following ingredients: other pesticides including fungicides and herbicides; herbicidal safeners; fertilizers and/or biocontrol agents. These ingredients may be added as a separate layer or alternatively may be added in the pesticidal coating layer.

The pesticide formulation may be applied to the seeds using conventional coating techniques and machines, such as fluidized bed techniques, the roller mill method, rotostatic seed treaters, and drum coaters. Other methods, such as spouted beds may also be useful. The seeds may be pre-sized before coating. After coating, the seeds are typically dried and then transferred to a sizing machine for sizing. Such procedures are known in the art.

The pesticide-treated seeds may also be enveloped with a film overcoating to protect the pesticide coating. Such overcoatings are known in the art and may be applied using conventional fluidized bed and drum film coating techniques.

In another embodiment of the present invention, a pesticide can be introduced onto or into a seed by use of solid matrix priming. For example, a quantity of the pesticide can be mixed with a solid matrix material and then the seed can be placed into contact with the solid matrix material for a period to allow the pesticide to be introduced to the seed. The seed can then optionally be separated from the solid matrix material and stored or used, or the mixture of solid matrix material plus seed can be stored or planted directly. Solid matrix materials which are useful in the present invention include polyacrylamide, starch, clay, silica, alumina, soil, sand, polyurea, polyacrylate, or any other material capable of absorbing or adsorbing the pesticide for a time and releasing that pesticide into or onto the seed. It is useful to make sure that the pesticide and the solid matrix material are compatible with each other. For example, the solid matrix material should be chosen so that it can release the pesticide at a reasonable rate, for example over a period of minutes, hours, or days.

The present invention further embodies imbibition as another method of treating seed with the pesticide. For example, plant seed can be combined for a period of time with a solution comprising from about 1% by weight to about 75% by weight of the pesticide in a solvent such as water. Preferably the concentration of the solution is from about 5% by weight to about 50% by weight, more preferably from about 10% by weight to about 25% by weight. During the period that the seed is combined with the solution, the seed takes up (imbibes) a portion of the pesticide. Optionally, the mixture of plant seed and solution can be agitated, for example by shaking, rolling, tumbling, or other means. After imbibition, the seed can be separated from the solution and optionally dried, for example by patting or air drying.

In yet another embodiment, a powdered pesticide can be mixed directly with seed. Optionally, a sticking agent can be used to adhere the powder to the seed surface. For example, a quantity of seed can be mixed with a sticking agent and optionally agitated to encourage uniform coating of the seed with the sticking agent. The seed coated with the sticking agent can then be mixed with the powdered pesticide. The mixture can be agitated, for example by tumbling, to encourage contact of the sticking agent with the powdered pesticide, thereby causing the powdered pesticide to stick to the seed.

The present invention also provides a transgenic corn seed that has been treated with a pesticide by the method described above.

The treated seeds of the present invention can be used for the propagation of corn plants in the same manner as conventional treated corn seed. The treated seeds can be stored, handled, sowed and tilled in the same manner as any other pesticide treated seed. Appropriate safety measures should be taken to limit contact of the treated seed with humans, food or feed materials, water and birds and wild or domestic animals.

In a preferred embodiment, the invention comprises an insect transgenic seed mix refuge strategy, comprising, e.g., 10% refuge (e.g non-insect protected transgenic) seed, combined with an insecticidal seed treatment. The combination of seed mix refuge strategy in combination with a seed treatment allows for protection of the non-transgenic plants in the mixture and provides a second mode of action for the transgenic seeds. The combination refuge strategy and second mode of action are optimal in delaying the onset of resistance development. This assumes that larvae would survive to adults on the non-transgenic plants and at the same time that these plants are sufficiently protected by the seed treatment. The seed treatment may be on all seed or only on the non-transgenic seed within the mix.

The phrase "seed mix refuge strategy" is intended to refer to a means for deploying into a field of crops some percentage of the seeds which sprout and develop into mature refuge plants but do not contain a transgene that is present in the crop seeds, thus allowing susceptible adults to survive. Although this strategy may be acceptable on low to moderate levels of insect pressure, under very high levels of insect pressure the non-protected plants, i.e. refuge plants, may be damaged such that this insect resistance management strategy is not commercially viable. By combining the mix seed refuge strategy with a seed treatment, the refuge plants are sufficiently protected but still allow for larval survivorship to adults, and the seed mix refuge strategy becomes commercially viable under all levels of insect pressure. At the same time, two modes of action are achieved, assuring the longest possible term for commercial viability and utility of the transgenic crop seeds with a minimal risk to the development of resistance races of insects.

One alternative to the approaches outlined above for achieving a seed-mix or seed-blend refuge composition would be to select a first transgenic crop seed to be mixed with a refuge seed to form a seed blend. The seed blend consists at least of a first transgenic crop seed, which contains at least a first transgene, and at least one type of refuge plant seed. The refuge plant seed can be uniform in nature, in that it is composed of a single type of seed from a single variety of plant, or can be non-uniform in nature and consist of two or more varieties of plant. Preferably the refuge seed is similar in variety (or agronomic characteristics) to the first transgenic crop seed. The refuge seed can be non-transgenic or can be transgenic. A refuge seed that is a transgenic seed can contain any transgene so long as it is not a transgene that is present in the first transgenic crop seed. It is preferable that a transgene in a transgenic refuge seed be a transgene selected from an insecticidal gene, a herbicide tolerance gene, a fungicide tolerance gene, and the like.

In the regulatory environment that currently exists today, obtaining the approval of an appropriate regulatory agency for commercialization of a recombinant plant generally requires that a percentage of all of the crop that is planted by a particular farmer intending to plant a crop containing a recombinant trait which effects the survival of particular insect pests be planted as a refuge of non-recombinant or non-transgenic crops, or crops which do not contain the ability to inhibit the development and growth of the particular insect pest by the same mode of action. In fact, it is preferred by the regulatory agencies that the refuge crop be planted with a non-transgenic crop, and it is further required that the refuge be planted as a block separate and apart from the recombinant crops. In addition, the percentage of the total crop planted is required to be at least 1% refuge, more preferably between from about 2 to about 5% refuge, even more preferably between from about 5% to about 10% refuge, and more preferably still between from about 10% to about 20% refuge or more depending on the amount of insect pressure expected for a particular geographic location and depending also on the type of crop plant subject to regulatory requirements. Such practices cause added expense for farmers in terms of their input into labor and financial expenses, and are difficult to police. Even though farmers are required to purchase enough non-recombinant seed to plant the required refuge along with any recombinant seed purchase, the added labor for planting and segregating the refuge and the likely lower yields within the refuge as a result of greater insect infestation is a disincentive for the farmer to comply with the regulatory requirements. Thus, a seed mix containing the requisite refuge amount of non-transgenic seed, and which is treated with an insecticide to protect the refuge plants from infestation, would be a commercially acceptable means for ensuring compliance with regulatory agency refuge strategies.

Advantages of a seed mix deployable refuge strategy over a block refuge strategy includes elimination of the issues around enforcement and compliance, simplicity, and complementarity with block refuge strategies required for other insect resistance traits. Furthermore by adding a seed treatment to the seed mix deployable refuge strategy, no plants are left unprotected in the field and a second mode of action is uniformly introduced to function along with the transgenic insect control means.

The seed mix deployable transgenic refuge strategy is particularly significant for corn rootworm resistant transgenic corn, for which a seed mix refuge strategy may be the only feasible means of deploying a refuge for the production of susceptible corn rootworms that will mate with any resistant individuals which may survive upon feeding on a corn rootworm resistant transgenic plant. By combining a seed treatment with the corn rootworm transgenic and non-transgenic seed in a mix, the seed mix refuge strategy would then be commercially viable, because the non-transgenic seed would be sufficiently protected by the seed treatment and still allow for sufficient numbers of larvae to survive to adults while continuing to provide for susceptible adult insects emerging from the field of crops.

This invention eliminates the necessity for grower application of chemical or other insecticides to the refuge to protect the plants as would be the case in a block refuge strategy. In the absence of seed treatment on the transgenic seeds in such a mix, the transgenic seeds sprout and send their roots outward and downward. Target insects which feed on these roots necessarily succumb to the levels of the insecticidal protein preferentially produced in the root tissue of the plant. In this scenario, the seeds comprising the non-transgenic refuge mixed uniformly into the seed mix deployable refuge mixture can either be treated with a chemical insecticide or left untreated. Of course the untreated refuge seed in the mixture would be entirely susceptible to insect infestation, generally resulting in a yield loss with respect to the percentage of refuge seed contained within the mixture.

Ideally, however, the refuge seed would be treated with a composition which contains at least one and perhaps two or more insecticidal agents selected from the group consisting of chemical insecticide and biologically derived insecticidal agents such as *Bacillus thuringiensis* insecticidal δ-endotoxin protein or vegetative insecticidal protein (VIP), *Bacillus sphaericus* insecticidal protein, *Bacillus laterosporus* insecticidal protein, insecticidal proteins derived from *Xenorhabdus* and *Photorhabdus* bacteria species, and insecticidal proteins which have been specifically demonstrated to be effective, including but not limited to Cry1's, Cry2's Cry5's, Cry9's and chimeras of these proteins for example for controlling lepidopteran species, and tIC851, CryET70, Cry22, and binary insecticidal proteins CryET33 and CryET34, CryET80 and CryET76, tIC100 and tIC101, CryET29, CryET37, TIC810, TIC812, and PS149B1. Treated refuge seeds within the mix would sprout when planted and the roots would grow outward and downward away from the soil surface. Commensurate with planting and exposure to the moisture in the soil, the treatment composition on the seed would disperse into the microenvironment of the seed in the soil, providing a decreasing concentration of insecticidal agent as a second mode of action through which the young root tissue would have to extend in order to be susceptible to insect feeding. Ordinarily, the microenvironment into which the insecticidal agents would disperse would be from about 1 to about 5 centimeters from the point of dispersion, or from about 1 to about 10 centimeters from the point of dispersion, said point of dispersion being defined as the centerpoint of the seed mass within the soil at the time of germination. Ordinarily, an insecticidally effective dose of the chemical or protein agent contained within the seed treatment would be required to extend outward for some distance from the centerpoint of seed mass within the soil at the time of germination. That effective dose would be required to be within the dispersal zone around the seed mass, generally being from about 1 to about 5 centimeters from the point of dispersion, and more preferably from about 1 to about 10 centimeters from the point of dispersion, and even more preferably from about 2 to about 10 centimeters from the point of dispersion.

One means of deploying a transgenic refuge into a field of recombinant crops would comprise a seed mixture comprising from about 1% to about 10% refuge seed or more preferably from about 5% to about 10% refuge seed. Alternatively, the refuge seed may comprise up to about 50% of the seed in a seed mixture. That is, the insect-protected transgenic seed might comprise from about 50% to about 60%, 70%, 75%, 80%, 90%, 95% or even up to about 99% of the seed mixture. This embodiment encompasses the treatment of all seeds contained within the mixture, such that the aforementioned dispersal zone around the center of mass of any of the seeds planted into the soil would suffice. It is also envisioned that regulatory requirements may mandate a refuge requirement greater than the aforementioned 20%, and it is intended that those greater requirements for refuge be included within the scope of this invention.

As noted previously, use of seed mixes for deployment of refuges for Insect Resistance Management (IRM) purposes have largely been directed towards management of rootworm-control traits. However the invention relates, in certain embodiments, to the finding that this approach may also be applied to resistance management for other pests, for instance including lepidopteran crop pests. Thus, highly mobile larvae of various lepidopteran pests, such as European cornborer, southwestern cornborer, corn earworm (aka cotton bollworm), pink bollworm, and fall armyworm, among others, may be subjected to resistance management via deployment of, for instance, seed compositions comprising a mix or blend of a lepidopteran-resistant seed, and a refuge seed. In particular, if two or more highly effective insecticidal proteins for control of a single pest species, such as a lepidopteran, are present in a crop line, then, for IRM purposes, the refuge planting may be accomplished by the planting of a seed composition comprising a mixture or blend of refuge seed and insect resistant seed, leading to growth of a refuge. In one embodiment, the refuge seed and insect resistant seed are of the same crop species, and, for instance, may be of the same variety, i.e. isogenic except for the presence or absence of the transgenic insect resistance trait(s). In such a case, the refuge would not be spatially structured, for instance as a row, strip, or block that is within, adjacent, or near a crop field, but instead would be spatially unstructured, consisting of plants dispersed within or among a crop or field.

Thus, including the refuge in the seed bag ("RIB") is one way of ensuring that all transgenic insect protected crop fields have associated refuge lacking insect protection. By blending insect protected seed with unprotected seed, refuge will be present in all fields independent of the product selected by a particular farmer. For example, corn seed consisting of a transgenic trait providing rootworm-protection could be blended with seed lacking a corn rootworm protection trait to provide a refuge included in the bag for rootworms that is independent of farmer practices.

In a particular embodiment, corn seed comprising event MON89034, expressing Cry1A.105 and Cry2Ab2, may be mixed with refuge seed (for instance at least 1% refuge seed) not comprising a gene encoding a Cry1 or Cry2 Bt toxin, or a related insecticidal toxin with lepidopteran activity, to produce a seed composition for use in the present invention. Some or all of the seed in such a composition may further be tolerant to application of a herbicide such as glyphosate. An insect resistance management plan, targeted against a lepidopteran insect pest and including a set of recommendations or requirements specifying the planting of insect resistant seed and as well as refuge seed according to the present invention is also an embodiment of the invention.

In another embodiment, a cotton seed composition comprising, for instance, events 281-24-236 and 3006-210-23, expressing Cry1F and Cry1Ac, and at least 1% refuge seed, as well as its use in an IRM program that describes use of a seed mixture or an "unstructured" refuge targeted against a lepidopteran pest are further embodiments of the invention. A cotton seed composition comprising a mixture of BOLLGARD II cotton seed, comprising events 531 and 15985 and expressing Cry1Ac and Cry2Ab proteins, and at least about 1% refuge seed is also an embodiment of the invention, as is the use of such a seed composition to meet IRM requirements for a lepidopteran pest, and an IRM plan that relates to use of such a seed composition. Other corn or cotton varieties comprising "stacked" transgenes that encode an insecticidal toxin may also be also be used to produce a seed composition of the present invention.

In certain embodiments, the crop may be corn, cotton, soybean, rice, or canola. In further embodiments, the transgenic crop seed and the refuge seed that comprise the seed mixture for use in an Insect Resistance Management program may be selected (e.g. matched) based on size and/or shape or other attribute, for instance prior to mixing the seeds, such that the insect resistant seed and the refuge seed are deliberately not distinguishable or are distinguishable as as they are planted. The seeds may also be processed in such a way, forinstance by application of a seed coating, as to make them indistinguishable or distinguishable as they are planted.

Further, the percentage of unprotected plants (i.e. lacking a protein, such as an insecticidal protein, directed toward the crop pest that is the subject of the resistance management recommendations) in such a seed mixture may be smaller than would have previously been required for growing pest-protected plants in accordance with resistance management requirements, but that lack two highly effective insecticidal toxins. Additionally, larger larvae of any of the target pest species that move from unprotected plants onto a protected plant would be killed by the combined activity of the highly effective insecticidal proteins. Therefore the problem of, for instance, lepidopteran larvae receiving by ingestion a sub-lethal dose of an insecticidal protein is much reduced or eliminated. This allows use of a non-spatially structured refuge, such as that created by use of the described seed mixture or blend, as an effective IRM tool for a transgenic crop product containing two or more such insecticidal traits.

In particular embodiments, in order to increase the effectiveness of the IRM refuge, refuge plants may be provided that are particularly attractive to a given crop pest, at least relative to the other plants grown from the seed mixture. For instance, the refuge plants may be selected based on their expected color, timing of silks or flowering, plant health, or vigour, to be nutritionally attractive to pests seeking to infest crop plants. The refuge plants may also comprise a transgene that results in the production of an insect attractant, such as a pheromone (e.g. U.S. Pat. No. 5,753,507). Particularly effective pheromones are those that act as a pest or species specific attractant, which is a more likely treatment for above ground pests. This use of such attractants is known in the art, for instance see Gregg et al. (U.S. Patent Publication 20050042316).

A refuge plant producing such an attractant, or having had such an attractant sprayed onto it would be particularly beneficial because it would cause the target pests to be particularly attracted to the vicinity of the crop field where the refuge crop plant is located. While this may in turn reduce the yield from the particular crop plant producing the attractant, it may also increase the overall yield from the refugia crop since the pest species attracted to this local vicinity may deposit their eggs onto a protected crop plant, resulting in the larvae feeding first on a transgenic plant tissue, and more effectively result in the decrease of pest pressure on the refuge.

Use of a seed mixture for insect resistance management may also be applied to multiple crop pests, including both lepidopteran and coleopteran pests. Rootworm larvae move less than lepidopteran larvae, and have been considered suitable targets for resistance management via a seed mixture or blend. The stacking of two or more highly effective insecticidal proteins for lepidopteran control, for instance as found in corn event MON 89034 which expresses Cry1A.105 and Cry2Ab2 effective against lepidopteran pests of corn, allows a seed mixture to be employed with additional coleopteran insecticidal protein(s) for control of both rootworm and lepidopterans, and can allow for the practice of an accepted IRM plan as well.

Thus, use of, for instance, corn seed comprising both events MON89034 and MON88017, which express Cry1A.105 and Cry2Ab2 for lepidopteran control and Cry3Bb* for rootworm control, in an insect resistance management plan would be a particular preferred embodiment of the invention, as would a seed blend or mixture comprising insect protected seed comprising both MON89034 and MON88017, and refuge seed. The invention also relates, in other embodiments, to a method of IRM comprising producing a seed composition comprising a mixture of another insect resistant seed line and a refuge seed line.

For instance, IRM use of a corn seed composition comprising, for instance, at least about 1% refuge seed mixed with events TC1507 (expressing Cry1F) and 59122-7 (expressing Cry34 and Cry35) for planting is an embodiment of the invention if an additional transgene encoding another lepidopteran active toxin, for instance Cry1Ab, is also present in the transgenic insect protected seed. A seed composition comprising such a mixture of seed is also an embodiment of the invention. Thus for instance, a seed composition, such as a corn seed composition, comprising refuge seed (not insect-protected) and for instance 10% refuge seed, blended with insect-protected crop seed that comprises transgenic events MON810, (expressing Cry1Ab), TC1507 (expressing Cry1F), and an additional transgene encoding a peptide toxin active against, for instance, corn rootworm, such as Cry34 and/or Cry35, is an embodiment of the invention, allowing deployment of an non-spatially-structured refuge crop for insect resistance management of both lepidopteran and coleopteran pests.

Yet another alternative embodiment is such a corn seed composition comprising at least about 1% refuge seed blended with insect-protected crop seed comprising transgenic events MON810, TC1507, and MON863. Likewise, use of event MON89034 may, for instance, be substituted for one or more of MON810 or TC1507; and 59122-7 may, for instance, be substituted for MON863 in any of the above crop seed compositions, as a seed composition is prepared for use with an IRM plan that permits use of a seed blend versus a lepidopteran pest, or a versus a combination of lepidopteran and coleopteran pests.

A blend of a stacked trait product (lepidopteran plus rootworm control insecticidal proteins) with non-insect-protected seeds that are, for instance, herbicide-tolerant, will allow effective insect resistance management for both insecticidal traits, meaning that farmers planting that product might not need to plant a structured refuge for either rootworms or lepidopteran pests. This would make the seed mixture approach a highly attractive solution in a county such as the U.S.A., where stacked products are becoming the products of choice for corn farmers. Refuge compliance issues would be eliminated for both traits.

A method for producing seed, such as a seed mixture comprising insect-protected seed and refuge seed, for use in an insect resistant management program is another embodiment of the invention. In particular embodiments, the seed may be corn seed, cotton seed, canola seed, soybean seed, or rice seed, among others. A method of IRM comprising planting such a seed mixture is also an embodiment of the invention. The seed may be selected for use in a mixture, for instance based on visual parameters including size and/or shape. The seed may further be processed, for instance by coating or pelleting to allow for more convenient use by planting machinery, or to provide a fungicide or insecticide component to the planted material, such as by a seed coating.

The invention further provides yield protection and may lead to increased yields relative planting the same proportion of unprotected seed as a separate block (i.e., in a traditional structured refuge). This can occur because unprotected plants in a field planted with an unstructured refuge will tend to be surrounded by insect-protected plants. This will decrease the average amount of damage occurring to unprotected plants because there will not be larvae moving over from other adjacent unprotected plants, as there would be in a block refuge and pest populations will tend to be smaller. Smaller pest populations on unprotected plants can mean less damage and higher yields. The yield protection may be greater when (a) the percentage of unprotected plants in the blend is lower and (b) when the protected plants provide higher levels of insect control. Both of these conditions can hold for highly effective products with multiple insecticidal proteins such as MON 89034 or for BOLLGARDII cotton, which expresses Cry1Ac and Cry2Ab. These conditions also would hold for other combinations of insecticidal proteins with similar properties. Studies with MON863 corn with corn rootworm protection demonstrate that a 10% refuge plant component in a crop grown from a seed mixture (e.g. 10% unprotected plants mixed with 90% Bt toxin producing plants) provides a greater yield than a comparable block of MON863 corn planted next to a 10% refuge block of unprotected corn. This shows that yield protection via an unstructured refuge can occur even with only a single insecticidal protein. A more effective product with multiple insecticidal proteins will confer much greater yield protection. This strategy increases the yield potential from the refuge plot (which is uniformly dispersed in and throughout the crop field) because refuge plants are surrounded by protected plants, and simultaneously reduces movement from infested plants. The reduced movement from infested plants onto the uninfested or less heavily infested refuge crops thus protects the crop produced from/by the refuge crop plant.

In other embodiments of the invention, the use of a seed mixture to meet an IRM requirement may also allow for more effective weed management in an insect protected crop field. Such a field may be very uniform in its resistance management needs because of the elimination of the need for a separately managed structured refuge. The strategy is applicable to a blend of seeds in which one type of seed in the blend contains one or more herbicide-tolerance genes, which also can be present on the insect-protected seed, enabling effective weed management using one or more herbicides. If two or more herbicide-tolerant genes are used, weeds resistant to one herbicide can still be managed with the second herbicide. Furthermore, herbicide applications can be more effectively timed because of the use of a seed mixture rather than spatially separate refuges. Combination of different herbicide tolerance genes together in a single transgenic plant makes such transgenic plants better/superior competitors versus weeds or versus any undesirable plant in a crop field. Plants that are transgenic for multiple herbicide tolerance traits may become more vigorous compared to weeds (where those weeds are undesirable plants, whether traditional weeds or volunteer crops remaining from earlier plantings) and thus more able to resist attack from pest infestation, whether by weeds or by insect, fungal, or nematode pressures.

EXAMPLES

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

Example 1

Production of transgenic corn seed effective against corn rootworm and treatment of such seed with imidacloprid (Gaucho®) and tefluthrin (Raze®).

Corn seeds were prepared to express amino acid sequence variant proteins of a Coleopteran inhibitory *Bacillus thuringiensis* Cry3Bb δ-endotoxin (Cry3Bb.11231 (MON853) or Cry3Bb.11098 (MON863)) by the methods described for these respective events in WO 99/31248. Such variant proteins have been shown to exhibit improved levels of bioactivity in controlling pests such as *Diabrotica* species. (U.S. Pat. No. 6,063,597).

Corn transformation event MON853 contains a nucleotide sequence which has not been optimized for plant expression. The insecticidal Cry3Bb protein variant produced by the MON853 event has been shown to exhibit improved insecticidal activity, in particular directed against corn rootworms. While it is not preferred that a nucleotide sequence encoding an insecticidal protein from *Bacillus thuringiensis* be introduced into a plant without first being modified to remove sequences which cause the resulting protein to be produced inefficiently, it is believed that the coding sequence within event MON853 functions to produce effective insecticidal activity in part because the length of the amino acid sequence which comprises a Cry3Bb variant protein is about half of a lepidopteran effective insecticidal *Bacillus thuringiensis* Cry protein, and because the MON853 variant protein, Cry3Bb.11231 has from about 3 to about 10 fold greater bioactivity against corn rootworms than the native Cry3Bb protein derived from *Bacillus thuringiensis*. Native *Bacillus thuringiensis* nucleotide sequences encoding truncated Cry proteins exhibiting lepidopteran inhibitory bioactivity are about the same size as the sequence encoding Cry3Bb variants exemplified in these examples herein, and have been shown to be expressed at very low but ineffective levels in some plants.

Corn transformation event MON863 contains a modified nucleotide sequence optimized for plant expression. The insecticidal Cry3Bb protein variant produced by the MON863 event, designated Cry3Bb.11098, has been shown to exhibit improved insecticidal activity, in particular directed against corn rootworms. MON863 exhibits better corn rootworm control than MON853 with or without seed treatment, more likely than not because the MON863 event contains a modified sequence encoding a variant Cry3Bb protein, 11098, similar in insecticidal activity to the variant Cry3Bb protein 11231 in event MON853, but which is expressed more efficiently from the modified coding sequence.

Corn seeds of the same hybrid species, with and without the respective transgenic events, were treated with either imidacloprid (available as Gaucho® from Bayer Corp.) or tefluthrin (available as Raze® from Wilbur-Ellis Co., Great Falls, Mt.; Walla Walla, Wash.) as follows. A seed treatment formulation of the desired pesticide was prepared by mixing a measured amount in water as a carrier and applying the formulation for one minute at room temperature to a measured weight of corn seed in a rotostatic seed treater. The respective weights of the pesticide preparation and the corn seed were calculated to provide the desired rate of treatment of pesticide on the seed. The pesticide was mixed into sufficient water to permit efficient distribution of the formulation to all of the seeds in the batch while minimizing loss of treatment formulation due to lack of uptake of the formulation by the seeds. Treated seeds were allowed to sit uncapped for at least four hours before planting.

When the seeds were treated with imidacloprid, a sufficient amount of Gaucho® 600 FS (containing 48.7% by weight imidacloprid; available from the Gustafson LLC) was thoroughly mixed into water to form a seed treatment formulation, and the formulation was applied to a weight of corn seed to provide treatment levels of 300 grams imidacloprid per 100 kg of seed (0.75 mg imidacloprid/kernel), or 400 grams imidacloprid per 100 kg of seed (1.0 mg imidacloprid/kernel).

When the seeds were treated with tefluthrin, a sufficient amount of Raze® 2.5 FS (containing 26.8% by weight tefluthrin; available from Wilbur-Ellis Co.,) was thoroughly mixed into water to form a seed treatment formulation, and the formulation was applied to a weight of corn seed to provide treatment levels of 300 grams active tefluthrin per 100 kg of seed (0.75 mg tefluthrin/kernel).

Example 2

Field trials for the determination of efficacy of transgenic event Cry3Bb.11231 in corn seed in combination with corn root worm pesticide seed treatments against western and northern corn rootworm.

Field trials were run in accordance with pertinent protocols and in conformance with USDA notification requirements. The purpose of the trials was to determine the efficacy of transgenic event Cry3Bb.11231 in corn seed in combination with corn root worm seed treatments against western and northern corn root worm.

For each growing site that was selected, the plot design included the following:
Row spacing: 30 inches
Plot size: 4 rows×20
Plant density: 2.0 seed/foot
Hybrid used: LH198×LH185 or RX670
Replicates: 4
Design: Randomized complete block
Locations: 4
Larvae source: natural infestations supplemented by artificial infestation of corn rootworm eggs at 400 eggs/ft (growth stage V2)

The following seed treatment combinations were used for each growing area:
No. Corn Seed Type Pesticide and amount (grams AI/100 kg seed or mg ai/kernel)
1 Isohybrid None, other than low levels for wire worm protection
2 Cry3Bb.11231 None, other than low levels for wire worm protection
3 Cry3Bb.11231 Gaucho® 600 FS @ 300 gm AI/100 kg or 0.75 mg AI/kernel
4 Cry3Bb.11231 Gaucho® 600 FS @ 400 gm AI/100 kg or 1.0 mg AI/kernel
5 Cry3Bb.11231 Raze® 2.5 FS @ 300 gm AI/100 kg or 0.75 mg AI/kernel
6 Isohybrid Force® 3 G @ 0.014 gm AI/m, or 0.15 oz AI/1000 ft row, applied as a 5" band on the soil surface at the time of planting.
7 Isohybrid Lorsban® 15 G (chlorpyrifos; available from DowElanco) @ 0.11 gm AI/m, or 1.2 oz AI/1000 ft row, applied as a 5" band on the soil surface at the time of planting.

All seed treatments with pesticides were carried out as described in Example 1. In seed treatment number 1 and 2, Gaucho® was used for wire worm protection, but at levels sufficiently low that it would be expected to have no effect on corn rootworms (i.e., at a treatment level of about 60 gm of active/100 kg seed or 0.16 mg active/kernel), otherwise, seed receiving treatment number 2 had only transgenic event Cry3Bb.11231 and no pesticide treatment that would be expected to be effective against corn rootworm.

For seeds having treatments numbered 3 through 5, the pesticides were applied by the methods described in Example 1. For seeds having treatment numbers 6 and 7, commercially available Force® 3 G and Lorsban® 15 G were applied to the soil in a 5" band at the time of sowing. The levels of application are as shown and are within the ranges recommended for standard commercial practice.

Corn seeds to be tested were planted and grown at four different locations across four Midwestern states in the United States corn belt according to the protocol described above.

The determination of damage by corn rootworm was made according to the following protocol. At stage V4-V6, an evaluation of early stand was made by counting the number of plants per acre. At stage VT-R1, an evaluation of corn rootworm damage was carried out by methods that are well known in the industry, and damage by corn rootworm was reported according to the Iowa 1-6 rating system. In that system, the root systems of 10 corn plants per plot are recovered and scored using the 1-6 rating scale, where: 1=no injury or only a few minor feeding scars, 2=feeding injury evident, but no roots eaten back to 1½ inches of the plant, 3=at least one root eaten off to within 1½ inches of the plant, but never an entire node of roots destroyed, 4=one node of roots eaten back to within 1½ inches of the plant, 5=two nodes (circles) of roots eaten back to within 1½ inches of the plant, 6=three nodes (circles) of roots eaten back to within 1½ inches of the plant.

TABLE 1

Corn rootworm damage to isohybrid corn plants having conventional surface banding treatments and corn plants having transgenic event Cry3Bb.11231 alone and in combination with seed treatment with selected pesticides at four growing locations.

| SEED NO. | SITE A | SITE B | SITE C | SITE D | MEANS ACROSS LOCATIONS |
|---|---|---|---|---|---|
| 1 | 4.3 | 4.0 | 4.0 | 4.2 | 4.1 |
| 2 | 2.5 | 2.4 | 2.2 | 2.0 | 2.3 |
| 3 | 2.1 | 2.3 | 2.5 | 1.9 | 2.2 |
| 4 | 1.8 | 2.3 | 2.2 | 1.8 | 2.0 |
| 5 | 2.3 | 2.3 | 2.6 | 1.8 | 2.2 |
| 6 | 2.7 | 2.1 | 2.6 | 1.9 | 2.3 |
| 7 | 3.3 | 2.4 | 2.5 | 1.8 | 2.5 |

From the data of Table 1, it can be seen that transgenic seeds that were treated with either imidacloprid or tefluthrin at any level were more resistant to corn rootworm damage than the transgenic seeds without such pesticide treatment. Moreover, all combination treatments (of transgenic event plus pesticide treatment) were more efficacious that conventional surface banding with either FORCE® or LORSBAN®.

Therefore, it can be concluded that the treatment of a corn seed having a transgenic event with either imidacloprid or tefluthrin provides improved resistance over that provided by either the transgenic event alone, or isohybrid seed that has also received a standard pesticide surface banding treatment at planting.

Example 3

Field trials for the determination of efficacy of transgenic event Cry3Bb.11231 in corn seed in combination with imidacloprid seed treatments against western and northern corn rootworm.

A field trial was established and completed in accordance with pertinent protocols and in conformance with USDA notification requirements. The purpose of the trial was to determine the efficacy of transgenic event Cry3Bb.11231 in corn seed in combination with corn rootworm seed treatments using imidacloprid.

For each growing site that was selected, the plot design included the following:

| | |
|---|---|
| Row spacing: | 30 inches |
| Plot size: | 4 rows × 20 |
| Plant density: | 2.0 seed/foot |
| Hybrid used: | LH198 × LH185 or RX670 |
| Replicates: | 4 |
| Design: | Randomized complete block |
| Locations: | 4 |
| Larvae source: | natural infestations supplemented by artificial infestation of corn rootworm eggs at 400 eggs/ft (growth stage V2) |

The following seed treatment combinations were used for each growing area:

| No. | Corn Seed Type | Pesticide and amount (grams AI/100 kg seed or mg ai/kernel) |
|---|---|---|
| 1 | Isohybrid | None, other than low levels for wire worm protection |
| 2 | Cry3Bb.11231 | None, other than low levels for wire worm protection |
| 3 | Cry3Bb.11231 | Gaucho ® 600 FS @ 300 gm AI/100 kg or .75 mg AI/kernel |
| 4 | Cry3Bb.11231 | Gaucho ® 600 FS @ 400 gm AI/100 kg or 1.0 mg AI/kernel |
| 5 | Cry3Bb.11231 | Raze ® 2.5 FS @ 300 gm AI/100 kg or .75 mg AI/kernel |
| 6 | Isohybrid | Force ® 3G @ 0.014 gm AI/m, or 0.15 oz AI/1000 ft row, applied as a 5" band on the soil surface at the time of planting. |
| 7 | Isohybrid | Lorsban ® 15 G (chlorpyrifos; available from DowElanco) @ 0.11 gm AI/m, or 1.2 oz AI/1000 ft row, applied as a 5" band on the soil surface at the time of planting. |

All seed treatments with pesticides were carried out as described in Example 1. In seed treatment number 1 and 2, Gaucho® was used for wire worm protection, but at levels sufficiently low that it would be expected to have no effect on corn rootworms (i.e., at a treatment level of about 60 gm of active/100 kg seed or 0.16 mg active/kernel), otherwise, seed receiving treatment number 2 had only transgenic event Cry3Bb.11231 and no pesticide treatment that would be expected to be effective against corn rootworm.

For seeds having treatments numbered 3 through 5, the pesticides were applied by the methods described in Example 1. For seeds having treatment numbers 6 and 7, commercially available Force® 3 G and Lorsban® 15 G were applied to the soil in a 5" band at the time of sowing.

The levels of application are as shown and are within the ranges recommended for standard commercial practice.

Corn seeds to be tested were planted and grown at four different locations across several Midwestern states in the United States corn belt according to the protocol described above.

The determination of damage by corn root worm was made according to the protocol described in Example 2.

TABLE 2

Corn rootworm damage to isohybrid corn plants and corn plants having transgenic event Cry3Bb.11231 alone and in combination with seed treatment with imidacloprid pesticide at different growing locations.

| TREATMENT | CORN ROOTWORM DAMAGE IN EACH IOWA CLASS (IOWA 1-6 SCALE) | | | | | | GRAND TOTAL | PERCENT OF CONTROL |
|---|---|---|---|---|---|---|---|---|
| | 1 | 2 | 3 | 4 | 5 | 6 | | |
| Isohybrid | 0 | 3 | 16 | 36 | 21 | 4 | 80 | 100 |
| Cry3Bb.11231 | 5 | 51 | 23 | 1 | 0 | 0 | 80 | 31.2 |
| Imidacloprid @ 400 g/100 kg of seed | 3 | 15 | 36 | 21 | 5 | 0 | 80 | 80.5 |
| Cry3Bb.11231 with Imidacloprid @ 400 gm/100 kg of seed | 13 | 53 | 14 | 0 | 0 | 0 | 80 | 18.2 |
| FORCE ® 3G surface band at planting | 3 | 58 | 34 | 3 | 0 | 0 | 98 | 39.2 |
| LORSBAN ® 15G surface band at planting | 6 | 39 | 38 | 16 | 1 | 0 | 100 | 57.1 |

Notes:
a. Data for the isohybrid control was taken as the same as determined for a related protocol that was carried out in an adjoining plot.

The data showed that both the transgenic event alone and seed treatment with imidacloprid alone provided some level of protection against corn rootworm damage above the untreated isohybrid control. At higher levels of damage (i.e., damage levels 4-6), corn having the transgenic event suffered 4.7% of the damage of the non-transgenic control. Since 4.7% would be considered to be about 5%, the Cry3Bb.11231 event was considered to be within a preferred effectiveness range of about 5% to about 50% of the damage of the non-transgenic control.

Imidacloprid seed treatment alone at 400 gm/100 kg was effective against corn rootworm damage, but the effectiveness of imidacloprid was lower than the effectiveness of the transgenic event alone. The combination of treatment with imidacloprid of the transgenic seed was more effective against rootworm damage than the pesticide treatment alone or the transgenic event alone. Moreover, the combination of Cry3Bb.11231 with imidacloprid at 400 gm/100 kg of seed provided better protection than the commercial standard treatment of either FORCE® or LORSBAN® applied as a surface band at planting.

The advantages of the present treatment of transgenic seed with imidacloprid include the simplification of planting, by removing the requirement for separate application of the pesticide. Furthermore, planting is easier and safer, since the planter does not have to handle a concentrated pesticide.

The combination of imidacloprid seed treatment with corn seed having a Cry3Bb.11231 transgenic event was tested for possible synergy at a level of rootworm damage of 3-6. In the first test, shown in Table 2, the percentage of test plants having damage levels of from 3 to 6, on the Iowa 1-6 Scale, was determined for the control and for seeds treated with the pesticide at two levels, and for seeds having the transgenic event, alone and in combination. The following formula was then used to calculate a "synergy threshold":

(% of control Cry3Bb.11231)*(% of control imidacloprid treatment)/100.

This threshold was compared against the percent of control for the treatment combination (i.e., Cry3Bb.11231 with imidacloprid @ 400 gm/100 kg). If the treatment combination percent of control was below the threshold, then it was concluded that there was synergy. If the treatment combination percent of control was above the threshold, then it was concluded that synergy was not demonstrated for that combination.

It was believed that the measurement of rootworm damage at higher damage levels (i.e., levels 3-6) is a useful indicator that correlates with subsequent yield loss due to such damage. The reason for this is that rootworm damage at levels 1 and 2 seldom causes corn plants to fall over and lodge, and such minimal root loss is not believed to reduce the number or weight of kernels per ear. However, root damage at levels of 3 and above increasingly causes lodging and loss of yield. Therefore, it is believed that the summed damage levels of 3-6 (and in some cases, 4-6 and 5 and 6), provides a useful indication of the effect of corn rootworm damage on subsequent corn yield.

TABLE 3

Efficacy of seed treatment with imidacloprid alone and in combination with corn transgenic event Cry3Bb.11231 against corn rootworm damage at levels 3-6 on the Iowa 1-6 Scale.

| TREATMENT | NUMBER OF PLANTS HAVING 3-6 DAMAGE LEVEL | PERCENT OF CONTROL | THRESHOLD SYNERGY |
|---|---|---|---|
| Untreated Control | 96.1 | 100 | — |
| Cry3Bb.11231 | 40 | 31.2 | — |
| Imidacloprid @ 400 gm/100 kg | 71.7 | 80.5 | — |
| Cry3Bb.11231 with imidacloprid @ 400 gm/100 kg | 24 | 18.2 | 25.1 |
| FORCE 3G as surface band | 40.7 | 39.2 | — |
| LORSBAN 15G as surface band | 60.8 | 57.1 | — |

This analysis indicated that the combination of the corn Cry3Bb.11231 transgenic event with seed treatment with imidacloprid at 400 gm/100 kg was synergistic and unexpectedly efficacious against corn rootworm damage at the 3-6 level. Accordingly, it was concluded that the combination of the transgenic event with the imidacloprid seed treatment provided significant advantages over the use of either method alone, and that such protection was unexpectedly superior in efficacy against severe damage by corn rootworm.

It was also believed to be noteworthy that the combination of imidacloprid and transgenic event provided protection against severe corn rootworm damage at levels that were far better than that provided by either FORCE® or LORSBAN® applied as surface bands.

Example 4

A field trial for the determination of efficacy of the combination of transgenic event Cry3Bb.11231 in corn seed in combination with tefluthrin (available as RAZE® from Wilbur-Ellis Company) could be carried out according to the same protocol as described in Example 3, except that tefluthrin would be substituted for imidacloprid in each case where imidacloprid was used at levels expected to be effective against corn rootworm (e.g., at levels of higher than 60 gm/100 kg seed). If desirable, it would be permissible to continue to use imidacloprid at levels of 60 gm/100 kg, or less, for wireworm protection.

It would be expected that the combination of tefluthrin seed treatment with a transgenic event in corn seed having effectiveness against corn rootworm would provide synergistic protection similar to that shown in Example 3 for the combination of imidacloprid and Cry3Bb.11231.

Example 5

This example illustrates the use of a seed mixture containing various ratios of transgenic and non-transgenic seeds to deploy a transgenic refuge, with or without seed treatments, provides an effective means for allowing adequate survival of susceptible corn rootworms in fields of recombinant crops to prevent or slow the rate of resistance evolution and still reduce economic loss due to corn rootworm infestation.

The western corn rootworm (WCR), *D. virgifera virgifera*, is a widely distributed pest of maize in North America. In many instances, insecticides are indiscriminately used to reduce their numbers below an economically damaging level. To assist in the reduction of insecticides used against the WCR, the inventors herein have utilized a transgenic line of maize expressing the Cry3Bb insecticidal protein. Upon ingestion by the rootworm, this protein forms pores in the midgut cells causing swelling and lysis of these cells and eventually death to the feeding worm. One concern is that the WCR will evolve resistance to the protein which will potentially spread throughout the rootworm's distribution and population. Deploying a transgenic refuge by planting seed mixtures of transgenic and non-transgenic maize may be a reliable resistance management strategy for controlling corn rootworms. The inventors herein have investigated the technical feasibility of a resistance management program that uses in-field seed mixes containing various proportions of transgenic and non-transgenic seed, i.e., T:NT, in combination with a new seed treatment technology to prevent substantial damage to non-transgenic maize provided in the mix. If effective, this methodology could provide growers with greater yields at lower cost and labor requirements, and could simultaneously provide a means for preventing or managing the development of resistant strains of CRW. The underlying assumption is that planting of a mix comprising transgenic vs. non-transgenic (T:NT) seed at the appropriate ratios allows adequate survival of susceptible CRW in the fields to prevent or slow the rate of resistance evolution and still reduce economic losses due to CRW infestation.

This method utilized a factorial design having five ratio levels of transgenic vs non-transgenic seed in a mix, including 100:0 T:NT, 90:10 T:NT, 80:20 T:NT, 60:40 T:NT, and 0:100 T:NT. Two levels of WCR egg infestation were utilized at the V2-V3 plant growth stage, either of 500 eggs per thirty centimeter row or 1000 eggs per thirty centimeter row, which were designated as low and high infestation rates, respectively. Two levels of seed treatment were utilized, similar to what was used in the examples above. One treatment level consisted of Gaucho (imidocloprid) at 60 grams per 100 kilogram of seed and was designated as WWST. The other treatment level consisted of clothianidine at 200 milligrams on non-transgenic (NT) seed, Gaucho on the transgenic seed (T), designated CRWST1, and 100% non-transgenic (NT) seed mix. Four additional treatments were used for comparison purposes only, and were not included at all in the ANOVA's. One of these additional treatments consisted of T80NT20 at a low and high level of egg infestation, with imidocloprid applied at 30 grams per 100 kilograms of seed on transgenic (T) seed and Gaucho on the non-transgenic seed (NT), designated as the CRWST2 treatments. Another of these additional treatments consisted of two 100% non-transgenic (NT) trials at low and high levels of egg infestation, treated only with Force3G insecticide, which is the conventional means presently in commercial use for treating corn rootworm infestation. All treatments were replicated four times over 96 plots, and the seeds were hand planted to verify the proper transgenic vs non-transgenic (T:NT) rations. Emergence cages covered five plants, exemplifying the total plot of T:NT at various ratios. A Hills & Peters 1-6 damage rating scale, as indicated herein, was used to score the damage to roots near the end of the adult emergence cycle, using ten plants per rep out of a total of 800 plants.

Over all of the treatments, significantly more female WCR emerged than male WCR (4972 female vs 2823 male), using a paired t-test, in which $t=-7.82$, $df=79$, and $P<0.0001$. It was determined that there were no significant interactions among seed treatments, egg rates, and ratios of transgenic to non-transgenic maize. Seed treatment had no significant effect on the mean number of WCR emerging, however, it was determined that significantly more ($F=18.65$, $df=1.57$, $P<0.0001$) WCR emerged from caged infested at the high level (4447 total, 111.2±19.4) than at the low level of infestation (3348 total, 83.7±18.3). The mean number of WCR emerging from the different seed ratios differed significantly ($F=105.34$, $df=4.57$, $P<0.01$). All pairwise comparisons were significantly different ($df=57$, $P<0.0001$) based on t-tests on Least Squares Means using Bonferroni adjustments to control Type 1 errors (alpha=0.05), except for WCR emerging from the T90:NT10 and T80:NT20 ratio studies. The fewest number of WCR emerged from the T100NT0 ratio study and the highest number from the T0NT100 ratio study. The mean number of WCR emerging from the T80NT20 maize treated blend with CRWST2 (29.3±6.2) was comparable to the mean number emerging from the T80NT20 maize (35.9±4.8) treated blend with CRWST1 and WWST. The mean number of WCR emerging from the maize treated with Force3G (98.3±16.6) was comparable to the mean number emerging from the T60NT40 ratio study (93.6±12.2). Seed treatment had no significant effect on mean root damage rating, however, it was determined that a significant interaction between egg infestation rates and ratios of transgenic to non-transgenic maize ($F=5.35$, $df=1.776$, $P<0.001$). Based on t-tests on Least Squares Means using Bonferroni adjustments to control Type 1 errors (alpha=0.05), most pairwise comparisons were significantly different ($df=776$, $P<0.0001$). Exceptions include root damage rating from the low egg infestation rate at T0:NT100 and high egg infestation rate at T0:NT100, low egg infestation rate at T100:NT0, and high egg infestation rate at T100:NT0. The lowest root damage ratings were obtained from the T100NT0 ratio studies and the highest root damage rating was observed in the T0NT100 ratio study. The mean root damage rating from the maize treated with CRWST2 (1.61±0.10) was comparable to the mean root damage rating from the T80NT20 ratio study (1.81±0.07). Similarly, the mean root damage rating from the maize treated with Force3G (2.81±0.09) was comparable to the mean root damage rating from the T60NT40 ratio study (2.74±0.09).

More females emerged than males. Whether this is due to differential mortality on the sexes caused by the transgenic maize or some other phenomenon is not clear. Further investigations into the sex ratio of WCR is necessary to elucidate any sexually biased effects caused by the transgenic maize.

The number of emerging WCR differed among the ratios of transgenic maize to non-transgenic maize. The ratios T100NT0, T90NT10, and T80NT20 were the most effective at reducing rootworm populations. These three ratios had the least number of emerged beetles. As expected, the non-transgenic maize had little or no controlling effect on beetle numbers. The CRWST1 had no significant impact on reducing the number of emerging WCR or on root damage rating. Similar numbers of WCR emerged from both the T60NT40 ratio studies and the maize treated with Force3G, which may explain the similar amount of damage to maize roots for these two treatments.

Root damage greatly exceeded economically acceptable levels (RDR 3.0) for the T0NT100 maize plots, and only slightly for the T60NT40 ratio studies at high egg infestation rates. The least amounts of root damage occurred to plants in the T100NT0, T90NT10, and T80NT20 ratio studies. Maize planted at these ratios never exceeded the economically damaging root damage rating level of 3.0 on the Iowa Hills & Peters scale.

One concern about the commercial release of transgenic maize for control of CRW is the evolution of resistance by the rootworms. One means for managing the development of resistance is to require that producers and growers plant a refuge to maintain resistant alleles at a low frequency. This disclosure illustrates a seed mix refuge option. The data in this example illustrates that a T90NT10 and a T80NT20 ratio seed mix maintained root damage levels below the economically damaging levels and produced similar numbers of adult beetles. A T60NT40 ratio only exceeded economically damaging levels under high levels of insect infestation and was comparable to the conventionally used insecticide Force3G. The combination of a seed treatment along with the deployment of refuge seed in a mix of transgenic seeds is therefore a useful strategy for prolonging the onset of resistance to either the seed treatment or to the recombinant insect inhibitory trait contained within the plant tissue.

These results demonstrate that all ratios including transgenic maize were as effective as the traditional method of applying insecticides to maintain WCR root damage levels below economically damaging levels. Most of the transgenic:non-transgenic ratios performed much better than the traditional method. Only the 100% non-transgenic maize had consistent root damage ratings exceeding the economic threshold. Using a seed mix of transgenic and non-transgenic seed in various proportions, in particular in combination with seed treatments providing a second mode of action, for planting in a crop in a field, can reduce the onset of resistance in the target insect pests.

Example 6

This example illustrates a few of the various combinations of types of first recombinant or first transgenic crop seed that can be present in a seed blend with various types of transgenic or non-transgenic refuge crop seed or other refuge seed. The skilled artisan will recognize the many various combinations available in the art based on the present disclosure.

A transgenic insect resistant crop seed that contains a transgene conferring herbicide tolerance to the plant grown from the transgenic crop seed is mixed in various proportions with a refuge seed. The refuge seed is also a transgenic seed but contains only a transgene conferring herbicide tolerance to a plant grown from the seed, such as resistance to glyphosate, resistance to basta, resistance to glufosinate, and the like, and is not transgenic with respect to any insect resistance trait. However, the refuge seed is not required to contain a transgene. For example a transgenic cotton crop seed containing a transgene encoding a Bt insecticidal resistance gene toxic to lepidopteran insect larvae is present in a seed blend with a refuge cotton seed that contains a recombinant gene that confers resistance to various concentrations of ROUNDUP herbicide when applied to the surface of the plants. The transgenic cotton crop seed containing the Bt insecticidal resistance gene also contains a recombinant gene that confers resistance to various concentrations of ROUNDUP herbicide. Both types of seeds may be coated with a seed treatment that contains a pesticidal agent that is different from the Bt insecticide present in the transgenic cotton crop seeds. The seeds are blended together and bagged and provided to a grower. The grower plants the seeds in a field, and the seeds sprout and develop into plants. Plants are sprayed with an appropriate herbicide to control volunteer growth and development and/or weed pest growth and infestation in the field. The herbicide tolerant insect sensitive plants grown from the refuge seed act as a refuge for cotton insect pest infestation, and are evenly dispersed throughout the field.

A first transgenic maize variety is transformed to contain a gene conferring resistance to a coleopteran insect, a gene conferring resistance to a lepidopteran insect, a gene conferring tolerance ROUNDUP herbicide, and a gene causing the lipid composition of the oil in the corn seed crop to be different than the oil composition in a native maize variety. Seeds of the first transgenic maize variety are blended together in a uniform mixture with refuge seeds. Refuge seeds may be a mixture of transgenic and non-transgenic seeds or a uniform composition of either transgenic or non-transgenic seeds. When refuge transgenic seeds are used, a mixture of refuge transgenic maize seed containing at least one gene conferring tolerance to the herbicide ROUNDUP and either no other transgene or only one other transgene selected from the group consisting of the same gene conferring resistance to a coleopteran insect that is present in the first transgenic maize variety and the same gene conferring resistance to a lepidopteran insect that is present in the first transgenic maize variety. All of the seeds comprising the refuge seeds have been coated with a seed treatment that contains an insecticide that confers at least a second mode of action different from either the transgene that confers coleopteran insect resistance or the transgene that confers lepidopteran insect resistance to the first transgenic maize variety. The first transgenic maize seed and the refuge seed are blended together and bagged and provided to a grower. The grower plants the seeds in a field, and the seeds sprout and develop into plants. Plants are sprayed with an appropriate herbicide to control volunteer growth and development and/or weed pest growth and infestation in the field. The herbicide tolerant, insect infestation sensitive plants grown from the refuge seed act as a refuge for maize insect pest infestation, and are evenly dispersed throughout the field.

Example 7

Initial corn seed compositions that comprise a crop seed containing two highly effective transgenes conferring lepidopteran insect pest resistance via distinct modes of action are obtained, and mixed in various proportions with a refuge seed. The refuge seed is isogenic to the crop seed, except that the refuge seed lacks the transgenes that confer insect resistance, and the proportion of refuge seed in each of the resulting compositions varies between 1% and 50%. The resulting seed compositions are planted, and grown, and the population and Bt toxin sensitivity of the targeted lepidopteran pest(s) is assessed, for instance by pest trapping or by noting the extent on plants of signs of pest feeding. As a control, the same number of each crop seed and refuge seed are planted according to IRM recommendations as adjacent or nearby, but spatially distinct, blocks or strips, and grown under similar conditions. The targeted lepidopteran pest population of the refuge blocks is calculated for each proportion of refuge/crop seed, and yields are measured, and compared to that of the correspondingly proportioned seed mix. Savings of time and costs associated with planting are noted, together with higher yields from the seed mixes compared to the corresponding crop/refuge block arrangements, and the population of lepidopteran pests and their descendants present in the seed mix plot(s) and the control plot(s) during this and subsequent growing seasons do not detectably differ with respect to sensitivity to either insecticidal toxin encoded by a transgene.

Example 8

A. Stacked Lepidopteran and Coleopteran Resistance Traits in a Seed Blend

A corn seed composition similar to the one described in Example 7 is obtained, except that the crop seed also comprises a transgenic event conferring resistance to corn rootworm. Similar results are obtained with respect to planting convenience, pest control, yield, and IRM.

B. Blended Lepidopteran and Coleopteran Resistance Traits

A corn seed composition similar to the one described in Example 8A is obtained, except that in this instance the lepidopteran and coleopteran insect resistance traits are not found in the same seed, and non-transgenic refuge seed is not detectably present. Thus, the lepidopteran-protected seed serves as refuge for a coleopteran pest, and the coleopteran-protected seed serves as the lepidopteran pest's refuge.

Example 9

Deployment of a spatially unstructured refuge may also be utilized as a method for enhancing the flexibility and effectiveness of weed management while deploying refuge seed. A transgenic insect protected corn seed and a refuge corn seed comprising one or more of the same transgenic or non-transgenic herbicide tolerance traits are blended in a defined ratio, as described for instance in Example 7, to obtain a resulting corn seed composition.

This results in an insect protected crop field that is uniform in its resistance management needs because of the elimination of the need for a separately managed structured refuge. The strategy is applicable to a blend of seeds in which one type of seed in the blend contains one or more herbicide-tolerance genes, which also can be present on the insect-protected seed, enabling effective weed management using one or more herbicides. If two or more herbicide-tolerant genes are used, weeds resistant to one herbicide can still be managed with the second herbicide. Furthermore, herbicide applications can be more effectively timed because of the use of RIB rather than separate refuges. A combination of different herbicide tolerance genes together in a single transgenic plant makes such transgenic plants superior competitors versus weeds or versus any undesirable plant in a crop field to which has been applied one or more of the corresponding herbicides.

LIBERTY herbicide (active ingredient glufosinate) is not systemic. Thus, a larger weed being targeted by pesticide applications would need a greater application or multiple applications to knock down, requiring that the farmer play with the application times/rates where stacked herbicide tolerance traits can cause stunting of weeds and a later herbicide application may thus not require as much of either herbicide. Plants that are transgenic for multiple herbicide tolerance traits become more vigorous compared to weeds (undesirable plants whether traditional weeds or volunteer crops remaining from earlier plantings) and thus more able to resist attack from pest infestation, whether by weeds or by insect, fungal, or nematode pressures.

All references cited in this specification, including without limitation all papers, publications, presentations, texts, reports, manuscripts, brochures, internet postings, journal articles, periodicals, and the like, are hereby incorporated by reference. The discussion of the references herein is intended merely to summarize the assertions made by their authors and no admission is made that any reference constitutes prior art. Applicants reserve the right to challenge the accuracy and pertinence of the cited references.

In view of the above, it will be seen that the several advantages of the invention are achieved and other advantageous results attained.

As various changes could be made in the above methods and compositions without departing from the scope of the invention, it is intended that all matter contained in the above description shall be interpreted as illustrative and not in a limiting sense.

REFERENCES

The following references, to the extent that they provide exemplary procedural or other details supplementary to those set forth herein, are specifically incorporated herein by reference.

U.S. Pat. No. 4,245,432; U.S. Pat. No. 4,272,417; U.S. Pat. No. 4,339,456; U.S. Pat. No. 4,372,080; U.S. Pat. No. 4,383,391; U.S. Pat. No. 4,465,017; U.S. Pat. No. 4,634,587; U.S. Pat. No. 4,735,015; U.S. Pat. No. 4,759,945; U.S. Pat. No. 4,766,203; U.S. Pat. No. 4,797,279; U.S. Pat. No. 4,910,016; U.S. Pat. No. 5,034,404; U.S. Pat. No. 5,080,925; U.S. Pat. No. 5,107,787; U.S. Pat. No. 5,245,040; U.S. Pat. No. 5,300,127; U.S. Pat. No. 5,328,942; U.S. Pat. No. 5,389,399; U.S. Pat. No. 5,554,445; U.S. Pat. No. 5,580,544; U.S. Pat. No. 5,622,003; U.S. Pat. No. 5,633,375; U.S. Pat. No. 5,661,103; U.S. Pat. No. 5,696,144; U.S. Pat. No. 5,753,507; U.S. Pat. No. 5,791,084; U.S. Pat. No. 5,834,447; U.S. Pat. No. 5,849,320; U.S. Pat. No. 5,849,320; U.S. Pat. No. 5,852,012; U.S. Pat. No. 5,876,739; U.S. Pat. No. 5,876,739; U.S. Pat. No. 5,877,012; U.S. Pat. No. 5,882,713; U.S. Pat. No. 5,891,246; U.S. Pat. No. 5,918,413; U.S. Pat. No. 5,939,356; U.S.

Pat. No. 5,952,358; U.S. Pat. No. 5,952,358; U.S. Pat. No. 6,023,013; U.S. Pat. No. 6,023,013; U.S. Pat. No. 6,060,594; U.S. Pat. No. 6,063,597;

U.S. Prov. Appln. 60/232,099; U.S. application Ser. No. 09/853,533

U.S. Publn. 20050042316

Agi et al., *J. Cotton Sci.,* 5:74-80, 2001

Agrios, In: *Plant Pathology,* 3rd Ed., Academic Press, 1988.

Armstrong et al., *Crop Sci.,* 35(2):550-557, 1995.

Bates et al., *Nature Biotechnol.,* 23:57-62, 2005.

Corn Rootworms, Field Crops Pest Management Circular #16, Ohio Pest Management & Survey Program, at the Ohio State web site ag.ohio-state.edu/~ohioline/icm-fact/fc-16.html Fehr, In: *Breeding Methods for Cultivar Development,* Wilcox (Ed.), American Society of Agronomy, Madison, Wis., 1987.

Hills and Peters, *J. Econ. Entomol.,* 64:764-765, 1971.

Hone and Whitely, *Microbiol. Rev.,* 53:242-255, 1989.

Jansens et al., *Crop Sci.,* 37(5):1616-1624, 1997.

Li et al., *Crop Protect. J.,* 25:940-948, 2006.

Mallet and Porter, *Proc. R. Soc. Lond. B,* 250:165, 1992.

McCutcheon's, In: *Emulsifiers and Detergents,* MC Publishing Company, Vol. 1, NJ, 1996.

McCutcheon's, In: *Functional Materials,* MC Publishing Company, Vol. 2, NJ, 1996.

McGahen et al., *Corn Insect Control: Corn Rootworm,* PENpages number 08801502, Factsheet available from Pennsylvania State University, State College, Pa., 1989.

Metcalf, In: *Destructive and Useful Insects,* Agricultural Sci. Pub. McGraw Hill Higher Education; 4$^{th}$ Rev. Ed., 1962.

Moellenbeck et al., *Nat. Biotechnol.,* 19:668-672, 2001.

PCT Appln. WO 00/66742; PCT Appln. WO 01/49834; PCT Appln. WO 98/13498; PCT Appln. WO 99/31248; PCT Appln. WO 99/31248; PCT Appln. WO 99/31248.; PCT Appln. WO 99/35913; PCT Appln. WO/98027218

Ramachandran et al., *Agron. J.,* 92:368-374, 2000.

Tabashnik, *Proc. Royal Soc. Series,* 5:7-12, 1994.

*The Pesticide Manual,* 11th Ed., Tomlin (Ed.), British Crop Protection Council, Surry, UK, 1997.

Vaughn et al., *Crop Sci.,* 45:931-938, 2005.

What is claimed is:

1. A method for deploying a refuge crop in a field of transgenic pest resistant crops, said method comprising the steps of
   a) blending transgenic, pest-resistant crop seeds comprising at least a first transgene, with refuge crop seeds comprising at least a second transgene;
   b) ensuring a uniform mixture of transgenic and refuge crop seeds is provided; and
   c) providing said mixture for planting in a field, wherein the mixture consists of from between about 99% and about 80% transgenic, pest-resistant crop seed;
   wherein said first transgene is insecticidal against a Lepidopteran insect and confers resistance to at least a first pest;
   wherein the first transgene and second transgene encode different *Bacillus thuringiensis* insecticidal δ-endotoxin proteins conferring pest resistance by different modes of action; and
   wherein the refuge seeds do not comprise the first transgene.

2. A method for deploying a refuge crop in a field of transgenic pest resistant crops, said method comprising the steps of
   a) blending transgenic, pest-resistant crop seeds comprising at least a first transgene, comprising at least a second transgene;
   b) ensuring a uniform mixture of transgenic and refuge crop seeds is provided; and
   c) providing said mixture for planting in a field, wherein the mixture consists of from between about 99% and about 80% transgenic, pest-resistant crop seed;
   wherein said first transgene is insecticidal against a Lepidopteran insect and confers resistance to at least a first pest;
   wherein the second transgene is different from the first transgene;
   wherein the refuge seeds do not comprise the first transgene; and
   wherein the second transgene confers resistance to said first pest with a different mode of action than does said first transgene.

3. A method for deploying a refuge crop in a field of transgenic pest resistant crops, said method comprising the steps of
   a) blending transgenic, pest-resistant crop seeds comprising at least a first transgene, with refuge crop seeds comprising at least a second transgene;
   b) ensuring a uniform mixture of transgenic and refuge crop seeds is provided; and
   c) providing said mixture for planting in a field, wherein the mixture consists of from between about 99% and about 80% transgenic, pest-resistant crop seed;
   wherein said first transgene is insecticidal against a *Lepidopteran* insect and confers resistance to at least a first pest;
   wherein the refuge crop seeds comprise a second transgene that confers pest resistance to a different pest and/or by a different mode of action than does the first transgene; and
   wherein said refuge crop seeds comprise at least two different transgenic varieties of the same crop species,
   wherein the first transgenic variety exhibits resistance to one or more *Lepidopteran* species and is a refuge crop for the second transgenic variety;
   wherein said second transgenic variety is different from the first transgenic variety; and
   wherein said second transgenic variety exhibits resistance to one or more pest species other than a *Lepidopteran* species and is a refuge crop for said first transgenic variety.

* * * * *